United States Patent [19]

Murase et al.

[11] Patent Number: 5,177,215
[45] Date of Patent: Jan. 5, 1993

[54] HETEROCYCLIC COMPOUNDS AND PHARMACEUTICAL USE THEREOF

[75] Inventors: Kiyoshi Murase, Saitama; Toshiyasu Mase, Chiba; Hiromu Hara; Kenichi Tomioka, both of Saitama, all of Japan

[73] Assignee: Yamanouchi Pharmaceutical Co., Ltd., Tokyo, Japan

[21] Appl. No.: 486,550

[22] Filed: Feb. 28, 1990

Related U.S. Application Data

[60] Division of Ser. No. 362,959, Jun. 7, 1989, Pat. No. 4,908,368, which is a division of Ser. No. 173,734, Mar. 25, 1988, Pat. No. 4,855,310, which is a continuation-in-part of Ser. No. 796,628, Nov. 8, 1985, abandoned.

[30] Foreign Application Priority Data

Nov. 12, 1984 [JP] Japan .................................. 59-238991
Oct. 1, 1985 [JP] Japan .................................. 60-219327

[51] Int. Cl.⁵ ................. C07D 255/02; C07D 235/02; C07D 309/16; A61K 31/41; A61K 31/415; A61K 31/35

[52] U.S. Cl. ................................. 548/255; 548/264.8; 548/305; 549/419

[58] Field of Search ................. 548/454, 263.2, 264.8, 548/305; 514/384, 359, 395, 451; 549/419

[56] References Cited

U.S. PATENT DOCUMENTS

| | | | |
|---|---|---|---|
| 4,216,149 | 8/1980 | Asato | 548/454 |
| 4,382,142 | 5/1983 | Takatori et al. | 548/139 |
| 4,411,905 | 10/1983 | Albrecht et al. | 514/384 |
| 4,642,132 | 2/1987 | Schirmer et al. | 71/90 |
| 4,803,211 | 2/1989 | Mase et al. | 514/361 |

FOREIGN PATENT DOCUMENTS

| | | |
|---|---|---|
| 0632553 | 12/1961 | Canada . |
| 0067685 | 12/1982 | European Pat. Off. . |
| 0084673 | 8/1983 | European Pat. Off. . |
| 2139623 | 11/1984 | United Kingdom . |

OTHER PUBLICATIONS

Merck, et al., "The Merck Index", 9th Ed., 1977, Merck & Co., Inc. Rahway, N.J., P. ONR-94.
Shen, et al., "The Development of Antiasthmatic Drugs", Part III, ed., D. R. Buckle, et al., Butterworth Publishers, Kent, England, 1982, pp. 316, 317, 331-335.

*Primary Examiner*—David B. Springer
*Attorney, Agent, or Firm*—Burgess, Ryan & Wayne

[57] ABSTRACT

Novel heterocyclic compounds shown by the general formula

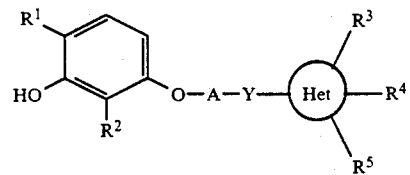

or the pharmaceutically acceptable salts thereof useful as medicament in particular as antagonist of slow reacting substance of anaphylaxis (SRS-A).

7 Claims, No Drawings

HETEROCYCLIC COMPOUNDS AND PHARMACEUTICAL USE THEREOF

This is a division, of application Ser. No. 362,959, filed Jun. 7, 1989 now U.S. Pat. No. 8,908,368 which is a division of U.S. Ser. No. 173,734 filed Mar. 25, 1988 now U.S. Pat. No. 4,855,310 which is a continuation in part of U.S. Pat. No. 796,628 filed Nov. 8, 1985, abandoned.

FIELD OF THE INVENTION

This invention relates to novel heterocyclic compounds shown by the following general formula (I) and the salts thereof use as medicaments, in particular as antagonist of slow reacting substance of anaphylaxis (SRS-A), and also a process of producing them;

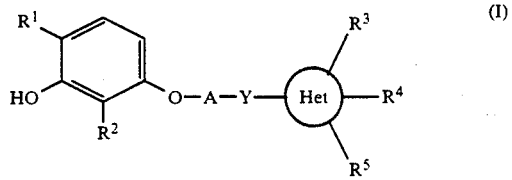

wherein, $R^1$ represents a lower acyl group; $R^2$ represents a lower alkyl group; A represents a lower alkylene group which may be substituted by a hydroxy group; Y represents an oxygen atom, a sulfur atom, a carbonylimino group (—CONH—), or an iminocarbonyl group (—NHCO—); Het represents a 5- or 6-membered heterocyclic ring having 1 to 3 hetero atoms selected from the group consisting of oxygen, sulfur and nitrogen, said heterocyclic ring may be fused with a benzene ring; $R^3$, $R^4$ and $R^5$, which may be the same or different, each represents a hydrogen atom, a lower alkyl group, a group shown by formula —$A^1$—$R^6$ (wherein, $A^1$ represents a lower alkylene group and $R^6$ represents a hydroxy group, a mercapto group, a carboxy group, or a lower alkoxycarbonyl group), a hydroxy group, a mercapto group, a lower alkoxy group, a lower alkylthio group, a group shown by formula $Y^1$—$A^2$—$R^7$ (wherein, $Y^1$ represents an oxygen atom or a sulfur atom; $A^2$ represents a lower alkylene group; and $R^7$ represents a carboxy group, a lower alkoxy-carbonyl group, a hydroxyaminocarbonyl group, a mono- or a di-lower alkylaminocarbonyl group, or an N-lower alkylhydroxyaminocarbonyl group), an oxo group (=O), a thioxo group (=S), an amino group, a group shown by formula —NH—$R^8$ (wherein, $R^8$ represents a carboxy lower alkyl group or a lower alkoxycarbonyl lower alkyl group), a group shown by formula —NH—CO—$R^9$ (wherein, $R^9$ represents a carboxy lower alkyl group, a lower alkoxycarbonyl lower alkyl group, a lower alkoxyphenyl lower alkoxycarbonyl lower alkyl group, a carboxy group, or a lower alkoxycarbonyl group), a carboxy group, or a group shown by formula —CO—$R^{10}$ (wherein, $R^{10}$ represents a lower alkoxy group); however, when Het is a heterocyclic ring fused with a benzene ring, Y is bonded to the heterocyclic ring.

BACKGROUND OF THE INVENTION

It is generally considered that in allergic asthma and other atopic diseases of man or anaphylactic shock in animals, various chemical mediators are released from lung and other tissues and cause difficulties in living bodies, such as the constriction of smooth muscles, e.g., bronchi, pulmonary artery, etc., and the enhancement of vascular permeability in the skin. As such chemical mediators, there are histamine and SRS-A. Histamine plays an important role in guinea pig anaphylactic shock but not in allergic asthma in man (Eiser, "Pharmacology and Therapeutics", 17, 239-250 (1982)), whereas a number of evidences suggest that SRS-A is the most important chemical mediator of allergic asthma in man (Brocklehurst, "Journal of Physiology", 151, 416-435(1960); Austen and Orange, "American Review of Respiratory Diseases", 12, 423-436(1975); Adams and Lichtenstein, "Journal of Immunology", 122, 555-562(1979)).

The development of the medicaments for prophylaxis, elimination and reduction of immediate hypersensitivity reactions was performed aiming at inhibiting the production and release of such chemical mediators or antagonizing the action of these chemical mediators. As an inhibitor of histamine release, disodium cromoglycate is well known and as an inhibitor of actions induced by histamine, various anti-histaminics are commercially available. On the other hand, SRS-A is known as a slow reactive and long acting chemical mediator while histamine is a rapid acting and short acting chemical mediator, and it has recently been recognized that SRS-A is a mixture of Leukotriens $C_4$, $D_4$ and $E_4$ the structure of which have been clarified by Dr. Samuelsson. SRS-A, i.e., Leukotriens are lipoxigenase products of polyunsaturated fatty acids (in particular, arachidonic acid) and it has been reported that SRS-A has various activities such as enhancement of mucus production, reduction of mucociliary transport, coronary artery constrictor action, reduction of cardiac contractility, etc., besides the aforesaid action in the character of chemical mediator in immediate hypersensitivity reactions.

To delineate the dynamic roles of SRS-A and to modulate its actions in various phthological conditions, obviously it would be highly desirable to have a specific and in vivo active receptor antagonist. Furthermore, it is clinically desirable to prepare an orally active compound. FPL 55712* of Fisons shows potent anti-SRS-A activity in isolated tissues (Augstein et al, Nature New Biol., 245, 215-217(1973)). However, its biological half life is very short and its absorption by oral route is very poor (Sheard et al, Mongr. Allergy, 12, 245-249(1977)).

(*)

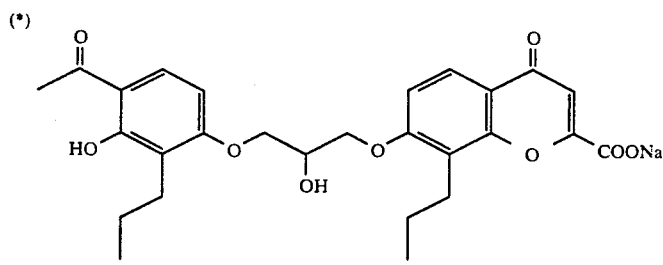

Accordingly, it has been desired to develop medicaments capable of inhibiting the production and release of SRS-A or medicaments capable of antagonizing these actions of SRS-A, in particular, the aforesaid medicaments effective in oral administration.

SUMMARY OF THE INVENTION

As the result of investigations for developing medicaments capable of inhibiting the production and release of SRS-A or medicaments capable of antagonizing the actions of SRS-A, the inventors have discovered that the compounds shown by general formula (I) described above and the salts thereof strongly antagonize the actions of SRS-A, are effective in oral administration, and show very weak toxicity, and the inventors have succeeded in accomplishing this invention based on the discovery.

The feature of the compound of this invention in chemical structure is on the point that a 5- or 6-membered heterocyclic ring having 1 to 3 hetero atoms is directly bonded to the terminal of the compound. That is, the compound of this invention has the chemical structural feature, as shown in the formula (I),

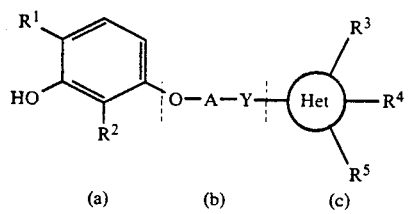

in the point that moiety (c) is a 5- or 6-membered heterocyclic ring having 1 to 3 hetero atoms and the heterocyclic ring is directly bonded to moiety (b).

Hitherto, in relation to the compounds of this invention, various compounds are known as, for example, above-described FPL 55712 of Fisons and as described in, for example, U.K. Patent No. 2,058,785. The U.K. patent discloses the compounds shown by the following the general formula;

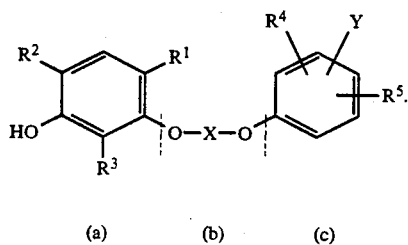

On these compounds, moiety (c) is a benzene ring or a benzene ring to which a heterocyclic ring is condensed and in each case the benzene ring is directly bonded to moiety (b). That is, compounds wherein the moiety (c) is a heterocyclic ring as the compounds of this invention are scarcely known. A tetrazole is reported in (Japanese Patent Publication (Unexamined) No. 164,344/84.

DETAILED DESCRIPTION OF THE INVENTION

The term "lower" in this specification means a straight or branched carbon chain of 1 to 6 carbon atoms.

Accordingly, the "lower alkyl group" includes a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, etc.

Also, the "lower acyl group" includes a formyl group, an acetyl group, a propionyl group, a butyryl group, an isobutyryl group, a valeryl group, an isovaleryl group, a pivaloyl group, a hexanoyl group, etc.

Furthermore, the "lower alkylene group" includes straight chain or branched alkylene groups having 1 to 6 carbon atoms, such as a methylene group, an ethylene group, a methylmethylene group

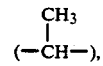

a trimethylene group, a 1-methylethylene group

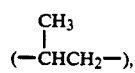

a 2-methylethylene group

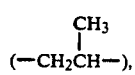

a tetramethylene group, a 1-methyltrimethylene group, a 2-methyltrimethylene group, a 3-methyltrimethylene group, a 1-ethylethylene group, a 2-ethylethylene group, a pentamethylene group, a 1-methyltetramethylene group, a 2-methyltetramethylene group, a 3-methyltetramethylene group, a 4-methyltetramethylene group, a hexamethylene group, etc. Practical examples of the "lower alkylene group" substituted by a hydroxy group are hydroxy lower alkylene groups that a hydrogen atom at an optional position of the above-described "lower alkylene group" is substituted by a hydroxy group, such as a hydroxymethylene group, a 1-hydroxyethylene group, a 2-hydroxyethylene group, a 1-hydroxytrimethylene group, a 2-hydroxytrimethylene group, a 3-hydroxytrimethylene group, a 1-hydroxy-2-methylethylene group, a 2-hydroxy-1-methylethylene group, a 1-hydroxytetramethylene group, a 2-hydroxytetramethylene group, a 3-hydroxytetramethylene group, a 4-hydroxytetramethylene group, a 2-hydroxy-1-methyltrimethylene group, a 2-hydroxy-3-methyltetramethylene group, a 2-hydroxypentamethylene group, a 4-hydroxypentamethylene group, a 2-hydroxyhexamethylene group, a 5-hydroxyhexamethylene group, etc.

Also, the "lower alkoxy group" includes straight chain or branched alkoxy groups having 1 to 6 carbon atoms, such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group, etc.

The "lower alkylthio group" are straight chain or branched alkylthio groups having 1 to 6 carbon atoms and includes a methylthio group, an ethylthio group, a propylthio group, as isopropylthio group, a butylthio group, an isobutylthio group, a sec-butylthio group, a tert-butylthio group, a pentylthio group, an isopentylthio group, a neopentylthio group, a tertpentylthio group, a hexylthio group, etc.

The "lower alkoxycarbonyl groups" is the groups ester-formed by straight chain or branched alcohols having 1 to 6 carbon atoms and carboxy group and includes a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group, etc.

Also, the term "mono- or di-lower alkylaminocarbonyl group" means an aminocarbonyl group of which one or two hydrogen atoms are substituted by the above-described "lower alkyl group". Practical examples of them are a monoalkylaminocarbonyl group substituted by a straight chain or branched alkyl group having 1 to 6 carbon atoms, such as a methylaminocarbonyl group, an ethylaminocarbonyl group, a propylaminocarbonyl group, an isopropylaminocarbonyl group, a butylaminocarbonyl group, an isobutylaminocarbonyl group, a pentylaminocarbonyl group, an isopentylaminocarbonyl group, a hexylaminocarbonyl group, etc.; a symmeteric dialkylaminocarbonyl group substituted by a straight chain or branched alkyl group having 1 to 6 carbon atoms, such as a dimethylaminocarbonyl group, a diethylaminocarbonyl group, a dipropylaminocarbonyl group, a diisopropylaminocarbonyl group, a dibutylaminocarbonyl group, a dipentylaminocarbonyl group, a dihexylaminocarbonyl group, etc.; and an asymmeteric dialkylaminocarbonyl group disubstituted by different alkyl groups each having 1 to 6 carbon atoms, such as an ethylmethylaminocarbonyl group, a methylpropylaminocarbonyl group, an ethylpropylaminocarbonyl group, a butylmethylaminocarbonyl group, a butylethylaminocarbonyl group, a butylpropylaminocarbonyl group, etc.

The term "N-lower alkyl-hydroxyaminocarbonyl group" means a hydroxyaminocarbonyl group

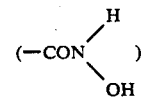

in which the hydrogen atom bonded to the nitrogen atom is substituted by the above-described "lower alkyl group". Practical examples thereof are an N-methylhydroxyaminocarbonyl group, an N-ethylhydroxyaminocarbonyl group, an N-propylhydroxyaminocarbonyl group, an N-isopropylhydroxyaminocarbonyl group, an N-butylhydroxyaminocarbonyl group, an N-isobutylhydroxyaminocarbonyl group, an N-pentylhydroxycarbonyl group, an N-isopentylhydroxyaminocarbonyl group, an N-hexylhydroxyaminocarbonyl group, etc.

The terms "carboxy lower alkyl group", "lower alkoxycarbonyl lower alkyl group", and "lower alkoxyphenyl lower alkoxycarbonyl lower alkyl group" mean the aforesaid "lower alkyl groups" an optional hydrogen atom of each of which is substituted by the "carboxy group", "lower alkoxycarbonyl group" or "lower alkoxyphenyl lower alkoxycarbonyl group", respectively. In addition, the "lower alkoxyphenyl lower alkoxycarbonyl group" means the aforesaid "lower alkoxycarbonyl group" an optional hydrogen atom of which is substituted by a phenyl group having the above-described "lower alkoxy group" at the ortho-, meta- or para-position.

Preferred examples of the 5- or 6-membered heterocyclic ring having 1 to 3 hetero atoms selected from an oxygen atom, a sulfur atom, and a nitrogen atom shown by (Het) are a

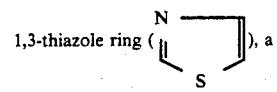

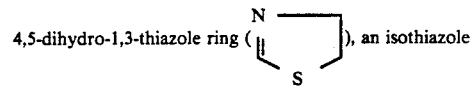

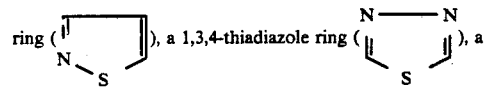

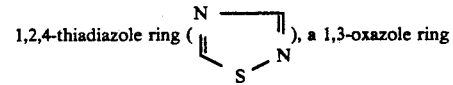

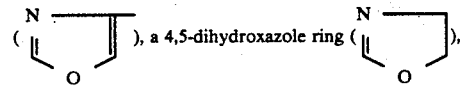

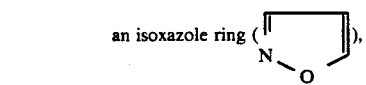

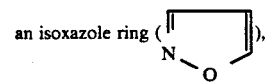

-continued

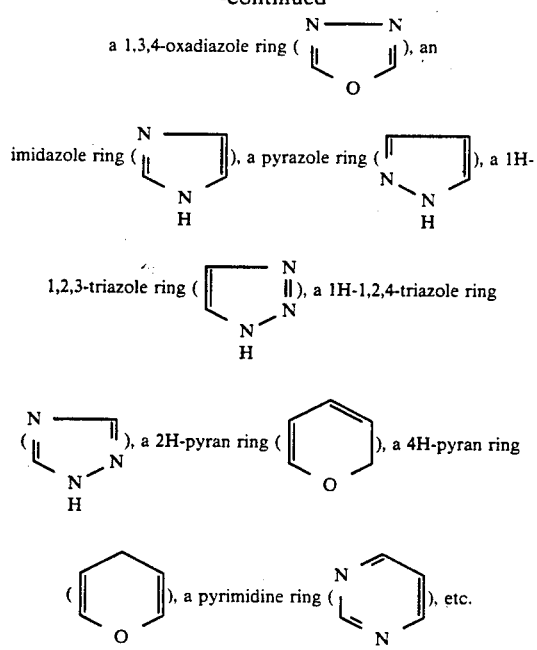

Also, practical examples of the condensates of these heterocyclic rings and a benzene ring are

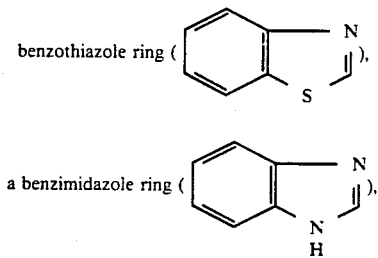

etc.

The heterocyclic ring has 1 to 3 substituents as $R^3$, $R^4$, and $R^5$ and also when the heterocyclic ring is condensed with a benzene ring, the substituents as $R^3$, $R^4$, and $R^5$ mean those bonded to the heterocyclic ring moiety. Therefore, according to the nature of the heterocyclic ring, there is a case that the substituents, $R^3$, $R^4$, and $R^5$ cannot bond to the carbon atom(s) of the ring and this case means that $R^3$, $R^4$ and/or $R^5$ is absence.

Practical examples of the substituents $R^3$, $R^4$, and $R^5$ of the hydrogen atom(s) of the heterocyclic ring are a lower alkyl group, a hydroxy-, mercapto-, carboxy- or lower alkoxycarbonyl-substituted lower alkylene group shown by the formula $-A^1-R^6$; a hydroxy group; a mercapto group; a lower alkoxy group; a lower alkylthio group; a carboxy-, lower alkoxycarbonyl-, mono or di lower alkylaminocarbonyl-, hydroxyaminocarbonyl-, or N-lower alkylhydroxyaminocarbonyl-substituted lower alkoxy or lower alkylthio group shown by the formula $-Y^1-A^2-R^7$; an oxo group; a thioxo group; an amino group; a carboxy- or lower alkoxycarbonyl-substituted lower alkylamino group shown by the formula $-NH-R^8$; a carboxy lower alkanoylamino group, a lower alkoxycarbonyl lower alkanoylamino group, a lower alkoxyphenyl lower alkoxycarbonyl lower alkanoylamino group, an oxaloamino group, or a lower alkoxyoxalylamino group each shown by the formula $-NH-CO-R^9$; a carboxy group; a lower alkoxycarbonyl group shown by formula $-CO-R^{10}$.

In addition, the "lower alkanoyl group" of the above-described "carboxy lower alkanoylamino group", "lower alkoxycarbonyl lower alkanoylamino group", and "lower alkoxyphenyl lower alkoxycarbonyl lower alkanoylamino group" means a straight chain or branched alkylcarbonyl group having 2 to 6 carbon atoms, such as an acetyl group, a propionyl group, a butyryl group, an isobutyryl group, a valeryl group, an isovaleryl group, a pivaloyl group, a hexanoyl group, etc.

The compound of this invention shown by the above-described general formula (I) includes optical isomers based on the existence of an asymmetric carbon; tautomers based on the kind of the heterocyclic ring or the existence of an oxo group, a hydroxy group, a thioxo group or a mercapto group; and cis, trans geometerical isomers based on two different substituents bonded to the saturated or partially saturated heterocyclic ring. The compound of this invention includes those isolated from these isomers and a mixture of them.

Some of the compounds of this invention form salts thereof and the compounds of this invention also include the salts of the compounds shown by the general formula (I). Examples of such salts are the salts with an inorganic base such as sodium, potassium, etc.; the salts with an organic base such as ethylamine, propylamine, diethylamine, triethylamine, morpholine, piperidine, N-ethylpiperidine, diethanolamine, cyclohexylamine, etc.; the salts with a basic amino acid such as lysine, ornithine, etc.; the ammonium salts; the salts with a mineral acid such as hydrochloric acid, sulfuric acid, phosphoric acid, hydrobromic acid, etc.; the salts with an organic acid such as acetic acid, oxalic acid, succinic acid, citric acid, maleic acid, malic acid, fumaric acid, tartaric acid, methansulfonic acid, etc.; and the salts with an acidic amino acid such as glutamic acid, aspartic acid, etc.

The compounds of this invention shown by general formula (I) can be prepared by various processes. Typical production process of the compounds are illustrated below.

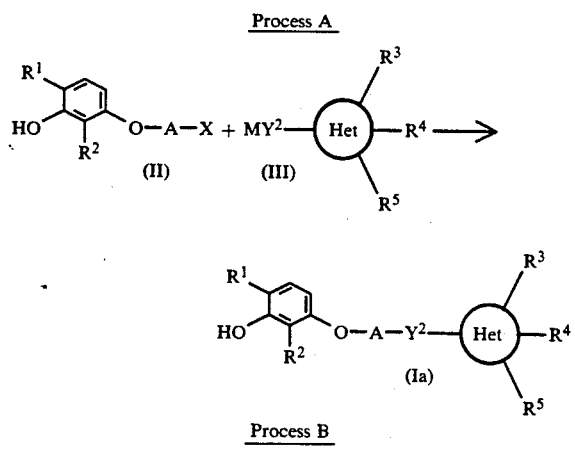

-continued
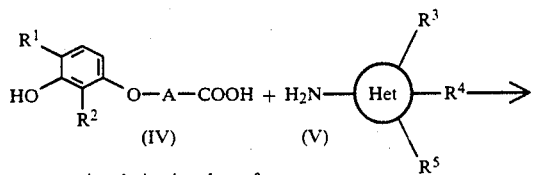
(IV)  (V)
or a reactive derivative thereof
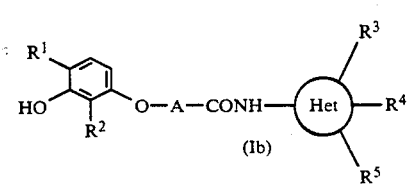
(Ib)
Process C
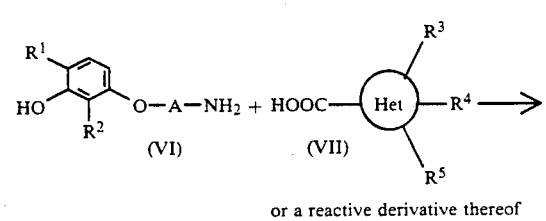
(VI)  (VII)
or a reactive derivative thereof
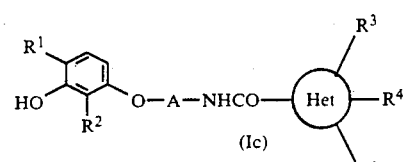
(Ic)
Process D
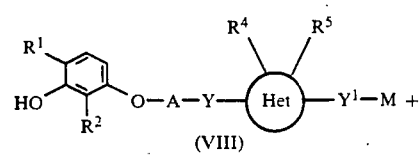
(VIII)
$$X-A^2-R^7 \longrightarrow$$
(IX)
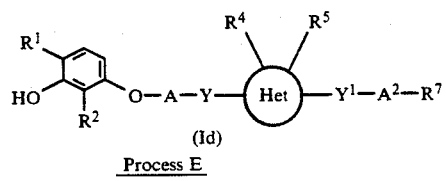
(Id)
Process E
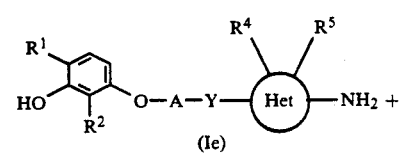
(Ie)
$$HOOC-R^9 \longrightarrow$$
(X)
or a reactive derivative thereof
-continued
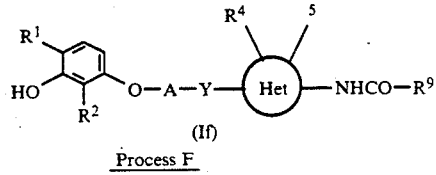
(If)
Process F
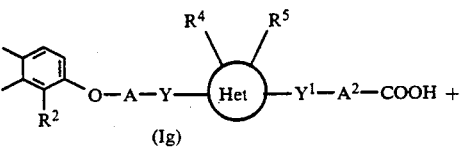
(Ig)
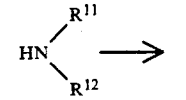
(XI)
or a reactive derivative thereof
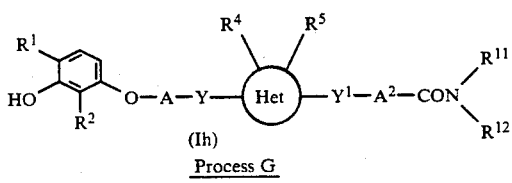
(Ih)
Process G
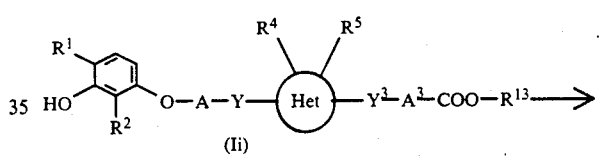
(Ii)
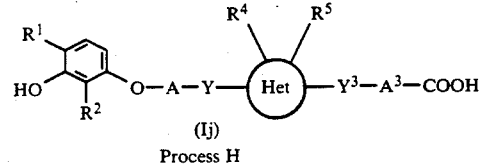
(Ij)
Process H
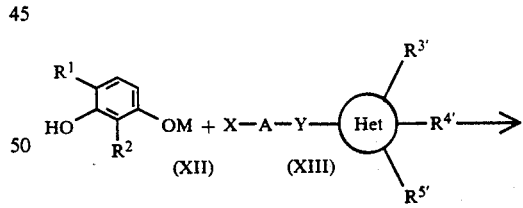
(XII)  (XIII)
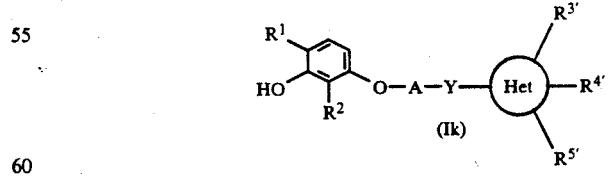
(Ik)
Process I
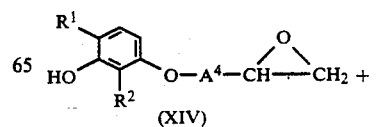
(XIV)

-continued

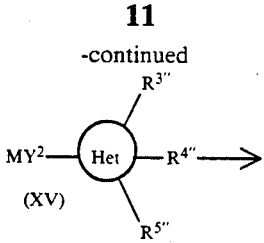
(XV)

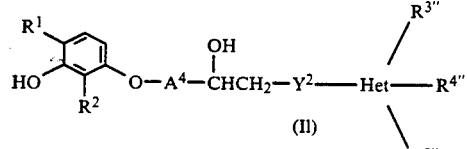
(II)

Process J

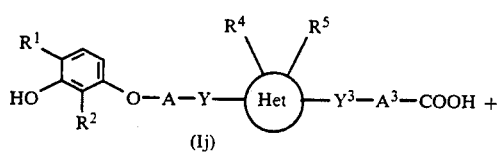
(Ij)

or a reactive derivative
thereof

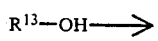
(XVI)

or a reactive derivative
thereof

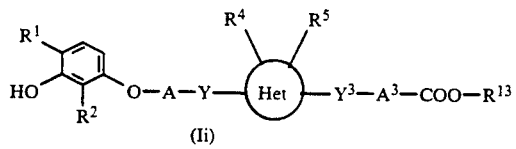
(Ii)

In the above formulae, $R^1$, $R^2$, A, Y, Het, $R^3$, $R^4$, $R^5$, $Y^1$, $A^2$, $R^7$, and $R^9$ have the same significance as defined above and other symbols have the following meanings:

X: A halogen atom.
M: A hydrogen atom or an alkali metal atom.
$Y^2$: An oxygen atom or a sulfur atom.
$R^{11}$: A hydrogen atom or a lower alkyl group.
$R^{12}$: A lower alkyl group or a hydroxy group.
$Y^3$: A single bond, an oxygen atom, a sulfur atom, or an imino group (—NH—).
$R^{13}$: A lower alkyl group.
$A^3$: A single bond, a lower alkylene group or, when $Y^3$ is an imino group; a carbonyl group or a carbonyl lower alkylene group.
$A^4$: A single bond or a lower alkylene group having 1 to 4 carbon atoms.
$R^{3'}$, $R^{4'}$, and $R^{5'}$: Same or different, a hydrogen atom, a lower alkyl group, a group shown by the formula —$A^1$—$R^{6'}$ (wherein, $A^1$ is the same as defined above and $R^{6'}$ represents a hydroxy group, a carboxy group, or a lower alkoxycarbonyl group), a hydroxy group, a lower alkoxy group, a lower alkylthio group, a group shown by the formula —$Y^1$—$A^2$—$R^{7'}$ (wherein, $Y^1$ and $A^2$ are the same as defined above and $R^{7'}$ represents a lower alkoxycarbonyl group, a hydroxyaminocarbonyl group, a mono- or di-lower alkylaminocarbonyl group, or an N-lower alkylhydroxyaminocarbonyl group), an oxo group (=O), an amino group, a group shown by the formula —NH—$R^{8'}$ (wherein, $R^{8'}$ represents a lower alkoxycarbonyl group), a group shown by the formula —NH—CO—$R^{9'}$ (wherein, $R^{9'}$ represents a lower alkoxycarbonyl lower alkyl group, a lower alkoxyphenyl lower alkoxycarbonyl lower alkyl group, or a lower alkoxycarbonyl group), a carboxy group, or a group shown by the formula —CO—$R^{10}$ (wherein, $R^{10}$ is the same as defined above).

$R^{3''}$, $R^{4''}$, and $R^{5''}$: Same or different, a hydrogen atom, a lower alkyl group, a group shown by the formula —$A^1$—$R^{6''}$ (wherein, $A^1$ is the same as defined above and $R^{6''}$ represents a hydroxy group, a carboxy group, or a lower alkoxycarbonyl group), a hydroxy group, a lower alkoxy group, a lower alkylthio group, a group shown by the formula —$Y^1$—$A^2$—$R^7$ (wherein, $Y^1$, $A^2$, and $R^7$ are same as defined above), an oxo group (=O), an amino group, a group shown by the formula —NH—$R^8$ (wherein, $R^8$ is the same as defined above), a group shown by the formula —NH—CO—$R^9$ (wherein, $R^9$ is same as defined above), a carboxy group, or a group shown by the formula —CO—$R^{10}$ (wherein, $R^{10}$ is the same as defined above).

In addition, a halogen atom includes an iodine atom, a bromine atom, a chlorine atom, etc., and an alkali metal atom includes sodium, potassium, etc.

Process A:

The compound of this invention shown by the general formula (I) wherein Y is an oxygen atom or a sulfur atom is produced by reacting a halogen compound shown by the general formula (II) and a hydroxy compound or mercapto compound shown by the general formula (III), or an alkali metal substitution product thereof.

The reaction is performed using the compound of the formula (II) and the compound of the formula (III) at an almost equimolar amount or at a slightly excessive amount in one of them in an organic solvent such as dimethylformamide, dimethylsulfoxide, methanol, ethanol, propanol, acetone, methyl ethyl ketone, tetrahydrofuran, chloroform, dioxane, etc., water, or a mixed solvent thereof.

When the hydroxy- or mercapto-substituted heterocyclic compound is used as the compound of the formula (III), the reaction is usually performed in the presence of a base and suitable examples of such a base are potassium carbonate, Triton B, potassium hydroxide, sodium hydroxide, sodium hydride, etc.

There is no particular restriction on the reaction temperature but the reaction is usually performed at room temperature or under heating.

Process B:

The compound of the formula (Ib) which is the compound of this invention shown by the general formula (I) wherein Y is a carbonylimino group (—CONH—) is produced by reacting a carboxylic acid shown by the general formula (IV) or the reactive derivative thereof and an amino compound shown by the general formula (V).

As the reactive derivatives of the compound of formula (IV), there are acid halide such as acid chloride, acid bromide, etc.; acid azides; active esters prepared with N-hydroxybenzotriazole or N-hydroxysuccinimide; symmetric acid anhydrides; mixed acid anhydrides prepared with alkyl chlorocarbonate or p-toluenesulfonyl chloride; etc.

When the compound of formula (IV) is used as a free carboxylic acid, it is advantageous to perform the reaction in the presence of a condensing agent such as dicyclohexylcarbodiimide, 1,1'-carbonyldiimidazole, etc.

The reaction is performed using the compound of the formula (IV) or the reactive derivative thereof and the compound of the formula (V) at an almost equimolar amount or at a slightly excessive amount in one of them in an organic solvent inactive to the reaction, such as pyridine, tetrahydrofuran, dioxane, ether, benzene, toluene, xylene, methylene chloride, dichloroethane, chloroform, dimethylformamide, ethyl acetate, acetonitrile, etc.

According to the kind of the reactive derivative, it is sometimes advantageous for smoothly performing the reaction to add a base such as triethylamine, pyridine, picoline, lutidine, N,N-dimethylaniline, potassium carbonate, sodium hydroxide, etc. Pyridine can be also used as the solvent.

The reaction temperature depends upon the kind of the reactive derivative and there is no particular restriction.

Process C:

The compound of the formula (Ic), which is the compound of this invention shown by the general formula (I) wherein Y is an iminocarbonyl group (—NHCO—) is produced by reacting an amine shown by the general formula (VI) and a carboxylic acid shown by the general formula (VII).

The reaction conditions, etc., are the same as those in Process B.

Process D:

The compound of the general formula (Id) wherein the heterocyclic ring is substituted by a lower alkoxy group, a lower alkylthio group, a lower alkoxycarbonyl lower alkoxy group, a lower alkoxycarbonyl lower alkylthio group, a carboxy lower alkoxy group, a carboxy lower alkylthio group, a lower alkoxycarbonyl lower alkoxy group, or a lower alkoxycarbonyl lower alkylthio group can be produced by reacting the compound of this invention shown by the general formula (VIII) wherein the heterocyclic ring is substituted by a hydroxy group or a mercapto group, or the alkali metal substitution product of the compound and a halogen compound of the formula (IX).

The reaction is performed almost the same as Process A.

When the compound of the formula (VIII) wherein the heterocyclic ring has plural of group shown by the formula —Y¹—M is used as the raw material, it is possible to prepare the compound wherein a group shown by the formula —A²—R⁷ is introduced to all of the group of —Y¹—M as the desired product.

Process E:

The compound of this invention wherein the heterocyclic ring is substituted by a carboxy lower alkanoylamino group, a lower alkoxycarbonyl lower alkanoylamino group, a lower alkoxyphenyl lower alkoxycarbonyl lower alkanoylamino group, an oxaloamino group or a lower alkoxyoxalylamino group can be produced by reacting a compound shown by the general formula (Ie) wherein the heterocyclic ring is substituted by an amino group and a carboxylic acid shown by the general formula (X) or the reactive derivative thereof.

The reaction conditions, etc., are almost the same as those in Processes B and C.

When the compound wherein the heterocyclic ring has plural amino groups is used as the raw material, the compound wherein all the amino groups are reacted can be obtained.

Process F:

The compound of this invention wherein the heterocyclic ring is substituted by a mono- or di-lower alkylaminocarbonyl lower alkoxy group, a mono- or di-lower alkylaminocarbonyl lower alkylthio group, an (N-lower alkyl)hydroxyaminocarbonyl lower alkoxy group, or an (N-lower alkyl)hydroxyaminocarbonyl lower alkylthio group is produced by reacting a carboxylic acid shown by the general formula (Ig) or the reactive derivative thereof and an amine shown by the general formula (XI).

The reaction is performed in the same method as the case of Processes B, C and E.

When the compound wherein the heterocyclic ring having plural carboxy groups is used as the raw material, the compound wherein the carboxy groups are wholly or selectively reacted can be obtained as the desired product.

Process G:

The free carboxylic acid compound shown by the general formula (Ij) can be easily produced by the hydrolysis of a corresponding ester compound shown by the general formula (Ii).

In the reaction, an ordinary process of performing hydrolysis in the presence of a base such as sodium carbonate, sodium hydroxide, etc., or an acid such as trifluoroacetic acid, hydrochloric acid, etc., can be applied.

When the compound wherein the heterocyclic ring has plural esters is used as the raw material, the compound wherein all the esters are hydrolyzed may be induced.

Process H:

The compound of this invention shown by the general formula (Ik) having no free mercapto group, carboxy group and reactive hydroxy group is produced by reacting a dihydroxybenzene derivative shown by the general formula (XIII) or the alkali metal substitution product thereof and a halogen compound shown by the general formula (XIII).

The reaction is performed in the same method as the case of Processes A and D wherein, in particular, the compound in which Y¹ or Y² is an oxygen atom is used.

Process I:

The compound of this invention wherein A is a 2-hydroxy lower alkylene group can be produced by reacting an epoxy compound shown by the general formula (XIV) and a hydroxy or mercapto compound (having no other mercapto group) or the alkali metal substitution product thereof.

The reaction is substantially the same as Processes A, D, and H. That is, the reaction is performed using the compound of formula (XIV) and the compound of formula (XV) at an almost equimolar amount or an excessive amount in one of them in an organic solvent inactive to the reaction, such as dimethylformamide, dimethylsulfoxide, methanol, ethanol, propanol, acetone, ethyl methyl ketone, tetrahydrofuran, chloroform, dioxane, etc. When a free hydroxy compound or mercapto compound is used as the compound of formula (XV), the reaction is performed in the presence of a base such as potassium carbonate, Triton B, potassium hydroxide, sodium hydroxide, sodium hydride, etc., under, preferably, water-free conditions.

Process J:

Contrary to the case of Process G, the ester compound shown by the general formula (Ii) is synthesized by reacting a carboxylic acid shown by the general formula (Ij) or the reactive derivative thereof and a lower alcohol or a reactive derivative of an alcohol component such as a lower alkyl halide, etc., shown by general formula (XVI).

The reaction can be easily accomplished by an ordinary process.

The compounds of this invention produced by the various processes described above can be isolated and purified by the application of an operation usually used in the field of the art, such as extraction, recrystallization, column chromatography, etc.

The compounds of this invention shown by general formula (I) strongly antagonize to the actions of SRS-A as described hereinbefore and hence are useful for the prophylaxis and treatment of various allergic diseases (e.g., bronchial asthma, allergic rhinitis, urticaria, etc.) caused by SRS-A and also ischemic heart diseases and ischemic brain diseases, inflamations, etc., caused by SRS-A.

Also, the compounds of this invention include, besides those having the activity antagonizing the actions of SRS-A, the compounds having the action of inhibiting the production and release of SRS-A and a bronchodilator action in addition to the aforesaid activity. Furthermore, the compounds of this invention are also useful as anti ulcer agent.

Inhibition of SRS-A- and LTD$_4$-induced contraction of guinea pig ileum and trachea Method: Male Hartley guinea-pigs, weighing 500 to 700 g were killed by a blow on the head. The ileum and tracheal strips prepared according to the method of Constantine (1965) were suspended with 1.0 g tension in an organ bath containing 10 ml of Tyrode's solution equilibrated with a mixture of 95% $O_2$ and 5% $CO_2$ at 37° C. The tissues were equilibrated for 60 min.; during this period the Tyrode's solution was replaced every 15 min. and the loading tension was adjusted to 1.0 g. The developed tension of the tissues was measured isometrically with a strain gauge transducer, and recorded on a Recticorder. Both the contractile response of the ileum to submaximal concentration of SRS-A (derived from guinea-pig lung) and the tracheal response to $10^{-8}$M LTD$_4$ were measured in the absence and then the presence of various concentrations of test compounds. The incubation time of the compounds was 20 min.

TABLE 1

| Example No. | Anti-SRS-A GP ileum IC50 (M) | Example No. | Anti-SRS-A GP ileum IC50 (M) |
| --- | --- | --- | --- |
| 2 | $1.8 \times 10^{-7}$ | 36 | $1.4 \times 10^{-7}$ |
| 7 | $1.1 \times 10^{-7}$ | 37 | $5.2 \times 10^{-8}$ |
| 21 | $6.0 \times 10^{-8}$ | 38 | $3.8 \times 10^{-8}$ |
| 23 | $1.5 \times 10^{-7}$ | 41 | $6.4 \times 10^{-8}$ |
| 24 | $1.9 \times 10^{-7}$ | 42 | $1.3 \times 10^{-7}$ |
| 26 | $1.2 \times 10^{-7}$ | 44 | $1.3 \times 10^{-7}$ |
| 27 | $1.9 \times 10^{-7}$ | 46 | $1.1 \times 10^{-7}$ |
| 33 | $9.1 \times 10^{-8}$ | 51 | $1.6 \times 10^{-7}$ |

TABLE 2

| Example No. | Anti-LTD$_4$ GP trachea IC50 (M) |
| --- | --- |
| 21 | $1.3 \times 10^{-7}$ |
| 38 | $2.3 \times 10^{-7}$ |

TABLE 2-continued

| Example No. | Anti-LTD$_4$ GP trachea IC50 (M) |
| --- | --- |
| 51 | $4.2 \times 10^{-7}$ |

Inhibition of SRS-A-mediated anaphylactic asthma in conscious guinea-pigs

Method: Male Hartley guinea-pigs, weighing 370 to 410 g were passively sensitized by intravenously injecting 1 ml/kg of rabbit anti-bovine serum albumin serum (PHA titer: 20480). Twenty-four hours after the sensitization, indomethacine (2 mg/kg), mepyramine (2 mg/kg) and propranolol (0.3 mg/kg) were injected into the saphenous vein 20, 5 and 5 min., respectively, prior to the antigen challenge. Then, animals were placed in an 11 liter chamber connected to a glass nebulizer, and 1% solution of bovin serum albumin was sprayed into the chamber for 30 seconds. The animals were exposed to the antigen aerosol for 2 min. and observed for 15 min. after challenge. The time from the start of inhalation to the onset of cough and the mortality were recorded. Test compounds were orally administered 30 min. before antigen challenge.

Result: Compound of Example 21 at 3 mg/kg p.o. tended to inhibit the SRS-A-mediated anaphylactic asthma in conscious guinea-pigs, but this effect was not significant (Table 3). At the doses of 10 mg/kg p.o. or higher, compound of Example 21 significantly inhibited the SRS-A-mediated anaphylactic asthma.

TABLE 3

Effect of Compound of Example 21 on SRS-A-mediated anaphylactic astham in conscious guinea-pigs[a]

| Compound[b] | Dose (mg/kg p.o.) | N | Time to onset of cough (sec) | Mortality |
| --- | --- | --- | --- | --- |
| Control | — | 8 | 293 ± 22 | 6/8 |
| Compound[c] | 3 | 8 | 377 ± 51 | 5/8 |
| Control | — | 8 | 281 ± 19 | 7/8 |
| Compound[c] | 10 | 8 | 397 ± 42* | 2/8* |
| Control | — | 8 | 281 ± 11 | 7/8 |
| Compound[c] | 30 | 8 | 457 ± 42** | 2/8* |

[a] Animals were pretreated with mepyramine (2 mg/kg i.v.), propranolol (0.3 mg/kg i.v.) and indomethacine (2 mg/kg i.v.) 5, 5 and 20 min., respectively, prior to antigen challenge.
[b] Test compound was orally administered 30 min. before antigen challenge.
[c] Compound of Example 21.
*p <0.05, **p <0.01: Significantly differed from the value of the control group.

Toxicity

The minimum fatal dose in the case of orally administering the compound of Example 21 to mice and rats was more than 1000 mg/kg in each case.

The compounds of this invention shown by the general formula (I) or the salts thereof can be orally or parenterally administered as they are or as medical compositions composed of these compounds and pharmaceutically permissible carriers or excipients (e.g., tablets, capsules, powders, granules, pills, ointments, syrups, injections, inhalants, suppositories, etc.). The dose is depends upon the patients, administrating routes, symptoms, etc., but is usually 0.1 to 500 mg, preferably 1 to 200 mg per adult per day and is orally or parenterally administered 2 or 3 times per day.

Then, the invention will be explained by the following example in detail.

In addition, the production examples of the raw material compounds used in these examples are shown in the following reference examples, wherein nPr means a n-propyl group.

REFERENCE EXAMPLE 1

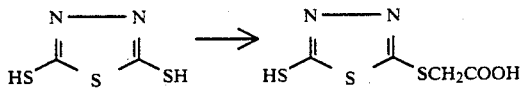

After stirring a mixture of 60 g of 2,5-dimercapto-1,3,4-thiadiazole, 25 g of potassium hydroxide, and 750 ml of ethanol for one hour at 70° C., 68 g of ethyl α-bromoacetate was added to the mixture and then the resultant mixture was refluxed for 2 hours. After cooling the reaction mixture, insoluble matters were filtered off and the filtrate thus formed was concentrated under reduced pressure. To the residue thus formed was added 600 ml of 10% sodium hydroxide. The mixture was stirred for one hour at 80° C. After cooling, the reaction mixture was acidified by the addition of concentrated hydrochloric acid (below pH 1) and crystals thus formed were collected by filtration, washed with water, and recrystallized from acetone to provide 60 g of [(5-mercapto-1,3,4-thiadiazol-2-yl)thio]acetic acid.

Melting point: 170° C.

REFERENCE EXAMPLE 2

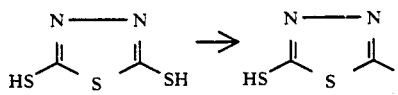

To a mixture of 3 g of 2,5-dimercapto-1,3,4-thiadiazole, 2.76 g of anhydrous potassium carbonate, and 10 ml of N,N-dimethylformamide was added 1 g of ethyl 4-bromobutyrate and the mixture was stirred overnight at room temperature. After addition of diluted hydrochloric acid to the reaction mixture, the product was extracted with ethyl acetate. The extract was washed with water, dried over anhydrous magnesium sulfate, and concentrated under reduced pressure. The residue thus obtained was applied to silica gel chromatography (using 200 ml of silica gel) and eluted with a mixture of toluene and ethyl acetate (9:1) to provide 0.95 g of ethyl 4-[(5-mercapto-1,3,4-thiadiazol-2-yl)thio]butyrate.

Melting point: 107° to 108° C.

REFERENCE EXAMPLE 3

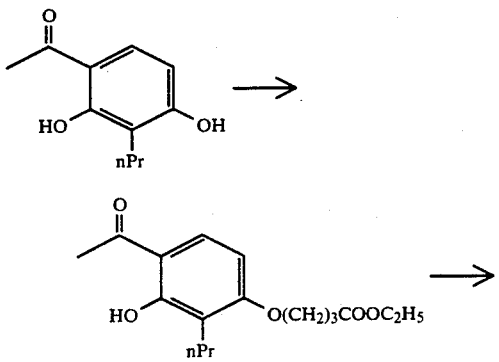

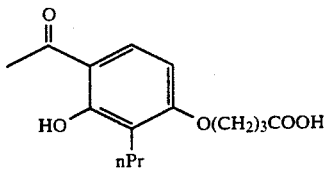

A mixture of 1.42 g of 2,4-dihydroxy-3-propylacetophenone, 2 g of ethyl 4-bromobutyrate, 1.5 g of potassium carbonate, and 10 ml of N,N-dimethylformamide was stirred overnight at room temperature. After addition of 100 ml of water to the reaction mixture, the product was extracted with 30 ml of toluene. The extract was washed with water, dried over anhydrous magnesium sulfate. The solvent was distilled off. The residue thus formed was applied to silica gel column chromatography and eluted with toluene to provide 1.5 g of ethyl 4-(4-acetyl-3-hydroxy-2-propylphenoxy)butyrate as an oily product. In a solution of 2 g of potassium hydroxide dissolved in 40 ml of 80% methanol was dissolved 1.3 g of the oily product and the solution was allowed to stand for one hour. To the reaction mixture was added 20 ml of water and methanol was distilled off under reduced pressure. The aqueous solution thus obtained was acidified by 5% hydrochloric acid and extracted by ethyl acetate. The extract thus formed was washed with water, dried over anhydrous magnesium sulfate. The solvent was distilled off to provided 1.1 g of 4-(4-acetyl-3-hydroxy-2-propylphenoxy)butyric acid.

Melting point: 138° to 139° C.

REFERENCE EXAMPLE 4

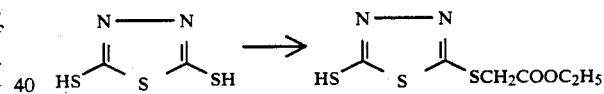

In a mixture of 9.66 g of sodium hydroxide, 14.6 ml of water, and 122 ml of methanol was dissolved 36.3 g of 2,5-dimercapto-1,3,4-thiadiazole. After cooling the mixture, a solution of 24.1 ml of ethyl bromoacetate and 24 ml of methanol was added to the mixture below 10° C. The resultant mixture was stirred for 3 hours at room temperature and cooled below 10° C. 43.5 ml of water and 400 ml of 50% methanol were successively added to the reaction mixture, whereby crystals precipitated, and the mixture was allowed to stand overnight at 4° C. The crystals were collected by filtration, washed successively with water and then 50% methanol, and dried to provide 42.5 g of ethyl [(5-mercapto-1,3,4-thiadiazol-2-yl)thio]acetate.

Melting point: 67° to 68° C.

REFERENCE EXAMPLE 5

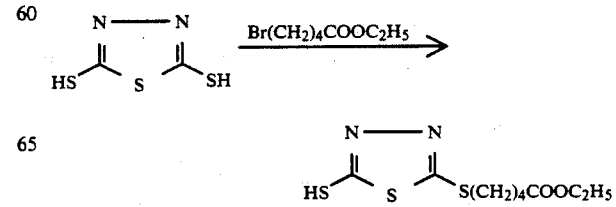

To a mixture of 10 g of 2,5-dimercapto-1,3,4-thiadiazole and 100 ml of methanol were added 2.6 g of sodium hydroxide and 5 ml of water. To the mixture was gradually added 9 g of ethyl 5-bromovalerate.

The resultant mixture was stirred for one hour at room temperature. The reaction mixture thus obtained was concentrated under reduced pressure. After addition of 100 ml of water to the residue, the product was extracted with ethyl acetate. The extract thus formed was washed with water, dried over anhydrous magnesium sulfate, and concentrated under reduced pressure. The residue was applied to silica gel column chromatography and eluted with a mixture of toluene and ethyl acetate (9:1) to provide 10 g of ethyl 5-[(5-mercapto-1,3,4-thiadiazol-2-yl)thio]valerate.

Melting point: 53° C.

REFERENCE EXAMPLE 6

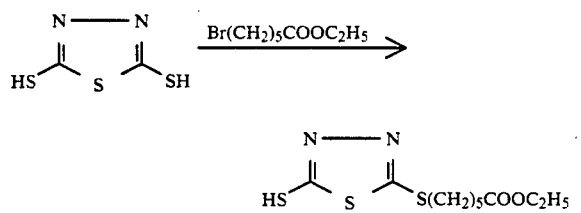

To a mixture of 7.6 g of 2,5-dimercapto-1,3,4-thiadiazole, 1.5 ml of water, 15 ml of methanol, and 2.0 g of sodium hydroxide was added 7.4 g of ethyl 6-bromohexanoate and the mixture was stirred for 2 hours at room temperature. After being acidified the reaction mixture thus obtained with diluted hydrochloric acid, 150 ml of water was added thereto. The mixture was extracted with toluene and the extract thus formed was washed with water, dried over anhydrous magnesium sulfate, and concentrated under reduced pressure. The residue thus formed was recrystallized from a mixture of toluene and n-hexane to provide ethyl 6-[(5-mercapto-1,3,4-thiadiazol-2-yl)thio]hexanoate.

Melting point: 79° to 80° C.

REFERENCE EXAMPLE 7

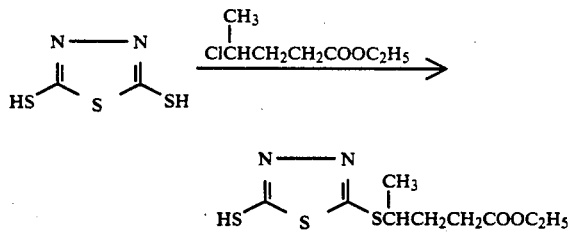

By following the same procedure as Reference Example 6 using 6.9 g of 2,5-dimercapto-1,3,4-thiadiazole and 5.8 g of ethyl 4-chlorovalerate as the starting materials, 1.5 g of ethyl 4-[(5-mercapto-1,3,4-thiadiazol-2-yl)thio]valerate was obtained as an oily product.

Nuclear magnetic resonance spectra (CDCl$_3$, TMS internal standard, ppm)

1.25(t, 3H), 1.45(d, 3H), 2.08(t, 2H), 2.52(t, 2H), 3.70(q, 1H), 4.15(q, 2H)

REFERENCE EXAMPLE 8

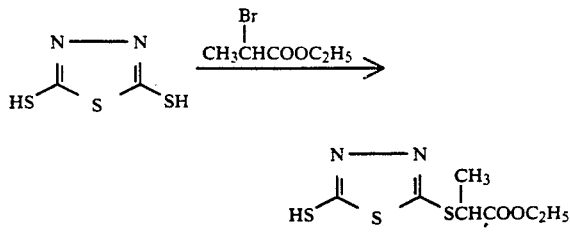

By following the same procedure as Reference Example 6 using 7.5 g of 2,5-dimercapto-1,3,4-thiadiazole and 5.8 g of ethyl 2-bromopropionate as the starting materials, 6.1 g of ethyl 2-[(5-mercapto-1,3,4-thiadiazol-2-yl)thio]propionate was obtained as an oily product.

Nuclear magnetic resonance spectra (CDCl$_3$, TMS internal standard, ppm)

1.28(t, 3H), 1.64(d, 3H), 4.0–4.80(m, 3H)

REFERENCE EXAMPLE 9

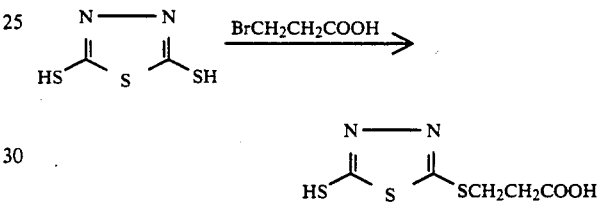

To a mixture of 1.5 g of 2,5-dimercapto-1,3,4-thiadiazole, 1.3 g of anhydrous potassium carbonate, and 20 ml of N,N-dimethylformamide was added 1.6 g of 3-bromopropionic acid, whereby the red color of the reaction mixture began to gradually fade and the reaction mixture became yellow. Then, the reaction mixture was poured into 100 ml of ice water and extracted with 30 ml of ethyl acetate three times. The extract thus obtained was washed with water and extracted with 20 ml of an aqueous solution of 5% sodium hydrogen carbonate two times. The extract was washed with ethyl acetate, acidified with diluted hydrochloric acid, and extracted with 30 ml of ethyl acetate three times and the extract thus obtained was washed with water, dried over anhydrous sodium sulfate, and concentrated under reduced pressure to provide 0.76 g of 3-[(5-mercapto-1,3,4-thiadiazol-2-yl)thio]propionic acid.

Melting point: 105° to 108° C.

REFERENCE EXAMPLE 10

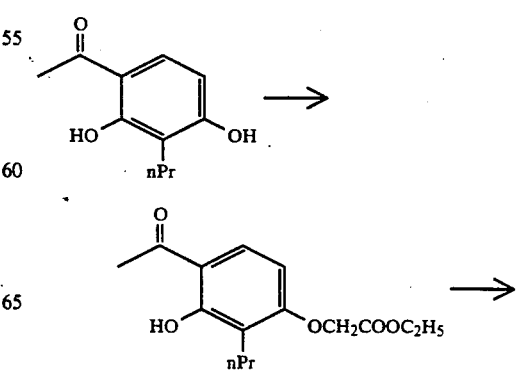

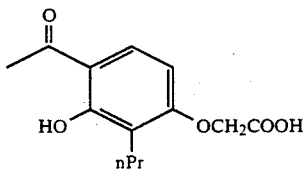

A mixture of 3 g of 2,4-dihydroxy-3-propylacetophenone, 2.5 g of ethyl bromoacetate, 2.3 g of anhydrous potassium carbonate, and 30 ml of methyl ethyl ketone was refluxed for 5 hours. Then, the solvent was removed under reduced pressure and after addition of 50 ml of toluene, the mixture was washed with water, a diluted aqueous solution of sodium hydroxide, and water successively, dried over anhydrous magnesium sulfate, and concentrated under reduced pressure. The residue thus formed was recrystallized from a mixture of toluene and n-hexane to provide 2.8 g of ethyl (4-acetyl-3-hydroxy-2-propylphenoxy)acetate (melting point: 66° to 66.5° C.).

A mixture of the product thus obtained, 20 ml of methanol, and 8 ml of a 2N aqueous solution of sodium hydroxide was stirred for 2 hours at 50° C. Then, the reaction mixture thus obtained was concentrated under reduced pressure, added 30 ml of water, and washed with toluene. The aqueous layer was acidified with diluted hydrochloric acid and extracted with ethyl acetate. The extract thus formed was washed with water, dried over anhydrous magnesium sulfate, and concentrated under reduced pressure. The residue thus formed was recrystallized from isopropanol to provide 2.3 g of (4-acetyl-3-hydroxy-2-porpylphenoxy)acetic acid.

Melting point: 140° to 141° C.

REFERENCE EXAMPLE 11

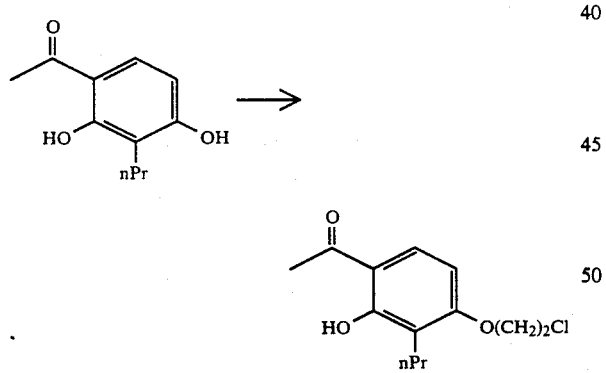

A mixture of 1 g of 2,4-dihydroxy-3-propylacetophenone, 1.1 g of 1-bromo-2-chloroethane, 0.75 g of anhydrous potassium carbonate, and 0.05 g of tetra-n-butylammonium bromide was refluxed for 3 hours with vigorous stirring. After cooling, 30 ml of toluene was added to the reaction mixture and the mixture was washed with a diluted aqueous solution of sodium hydroxide, washed with water, dried over anhydrous magnesium sulfate, and concentrated under reduced pressure. The residue thus formed was recrystallized from isopropanol to provide 0.46 g of 4-(2-chloroethoxy)-2-hydroxy-3-propylacetophenone.

Melting point: 73° to 74° C.

| Elemental analysis for $C_{13}H_{17}O_3Cl$: | | | |
|---|---|---|---|
| | C | H | Cl |
| Calculated: | 60.82% | 6.67% | 13.81% |
| Found: | 60.67% | 6.72% | 13.76% |

REFERENCE EXAMPLE 12

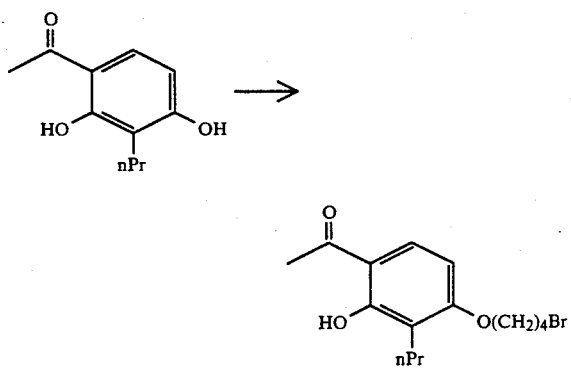

By following the same procedure as Reference Example 11 using 1 g of 2,4-dihydroxy-3-propylacetophenone and 4.5 g of 1,4-dibromobutane as starting materials followed by purification by silica gel column chromatography (eluant: toluene), 1.3 g of 4-(4-bromobutoxy)-2-hydroxy-3-propylacetophenone was obtained as an oily product.

Nuclear magnetic resonance spectra (CDCl$_3$, TMS internal standard, ppm)

0.95(t, 3H), 1.10–1.80(m, 2H), 1.80–2.20(m, 4H), 2.58(s, 3H), 2.64(t, 2H), 3.52(t, 2H), 4.08(t, 2H), 6.42(d, 1H), 7.58(d, 1H), 12.7(s, 1H).

REFERENCE EXAMPLE 13

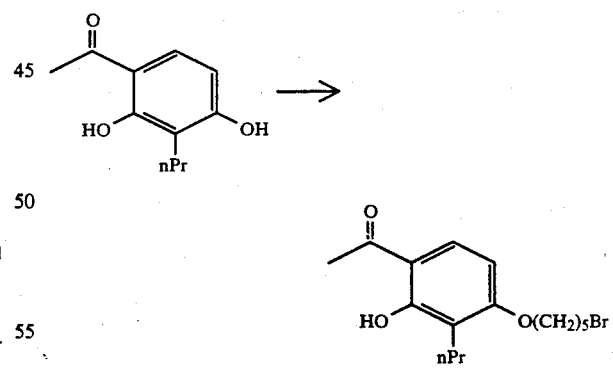

By following the same procedure as Reference Example 12 using 1 g of 2,4-dihydroxy-3-propylacetophenone and 4.7 g of 1,5-dibromopentane as the raw materials, 1.3 g of 4-(5-bromopentyloxy)-2-hydroxy-3-propylacetophenone was obtained as an oily product.

Nuclear magnetic resonance spectra (CDCl$_3$, TMS internal standard, ppm)

0.94(t, 3H), 1.30–2.10(m, 8H), 2.56(s, 3H), 2.64(t, 2H), 3.46(t, 2H), 4.40(t, 2H), 6.42(d, 1H), 7.58(d, 1H), 12.72(s, 1H).

REFERENCE EXAMPLE 14

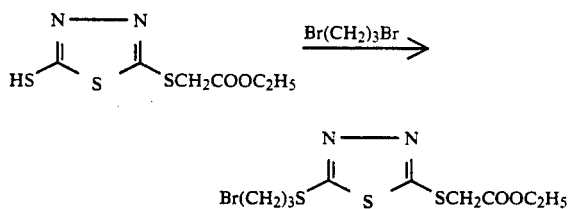

A mixture of 3 g of ethyl [(5-mercapto-1,3,4-thiadiazol-2-yl)thio]acetate, 9 g of 1,3-dibromopropane, 2.02 g of anhydrous potassium carbonate, 0.01 g of tetra-n-butylammonium bromide, and 20 ml of methyl ethyl ketone was vigorously stirred for 3 hours at 60° C. Toluene was added to the reaction mixture and the resultant mixture was washed with water, dried over anhydrous magnesium sulfate, and concentrated under reduced pressure. The residue thus formed was applied to silica gel column chromatography and eluted with a mixture of toluene and ethyl acetate (9:1) to provide 1.35 g of ethyl [[5-(3-bromopropyl)thio-1,3,4-thiadiazol-2-yl]thio]acetate.

Melting point: 118° to 120° C.

EXAMPLE 1

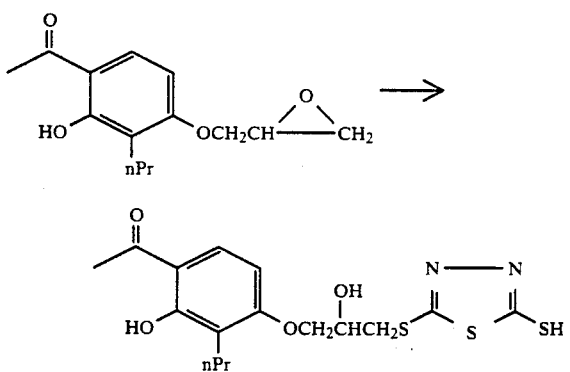

To a mixture of 600 mg of 2,5-dimercapto-1,3,4-thiadiazole, 560 mg of anhydrous potassium carbonate, and 10 ml of N,N-dimethylformamide was added 250 mg of 4-(2,3-epoxy)propoxy-2-hydroxy-3-propylacetophenone and the resultant mixture was stirred overnight at room temperature. To the reaction mixture thus obtained was added diluted hydrochloric acid and the product was extracted with toluene. The extract thus obtained was washed with water, dried over anhydrous magnesium sulfate, and concentrated under reduced pressure. The residue was applied to silica gel column chromatography and eluted with a mixture of toluene and ethyl acetate (4:1) to provide 260 mg of 2-hydroxy-4-[2-hydroxy-3-[(5-mercapto-1,3,4-thiadiazol-2-yl)thio]propoxy]-3-propylacetophenone as an oily product.

Nuclear magnetic resonance spectra (CDCl$_3$, TMS internal standard, ppm)

0.92(t, 3H), 1.2–1.8(m, 2H), 2.56(s, 3H), 2.63(t, 2H), 3.48(dd, 2H), 4.0–4.2(m, 2H), 4.2–4.6(m, 1H), 6.42(dd, 1H), 7.61(d, 1H), 12.7(s, 1H).

EXAMPLE 2

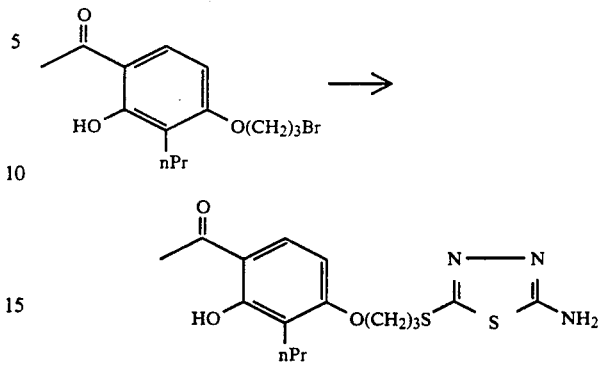

A mixture of 2 g of 4-(3-bromopropoxy)-2-hydroxy-3-propylacetophenone, 1.6 g of 2-amino-5-mercapto-1,3,4-thiadiazole, 1.6 g of potassium carbonate, and 20 ml of N,N-dimethylformamide was stirred for one hour at 20° to 30° C. and after addition of 100 ml of water to the reaction mixture thus obtained, the product was extracted with ethyl acetate. The extract was washed with water, dried over anhydrous magnesium sulfate, and then the solvent was distilled off. The residue thus formed was applied to silica gel column chromatography and eluted with toluene to provide 2.3 g of 4-[3-[(5-amino-1,3,4-thiadiazol-2-yl)thio]propoxy]-2-hydroxy-3-propylacetophenone.

Melting point: 144° to 145° C.

| Elemental analysis for C$_{16}$H$_{21}$N$_3$O$_3$S$_2$: | | | |
| --- | --- | --- | --- |
| C | H | N | S |
| Calculated: 52.29% | 5.76% | 11.43% | 17.45% |
| Found: 52.09% | 5.71% | 11.58% | 17.61% |

EXAMPLES 3 TO 13

By following the same procedure as Example 2 following compounds were obtained.

EXAMPLE 3

Starting compound:

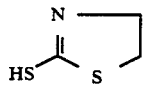

Desired compound: 2-Hydroxy-3-propyl-4-[3-[(2-thiazolin-2-yl)thio]propxy]acetophenone

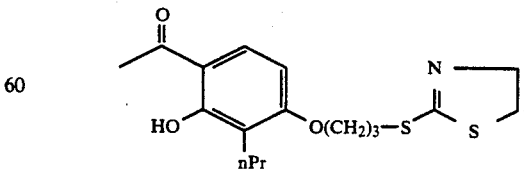

Physicochemical properties:
1) Oily product
ii) Nuclear magnetic resonance spectra (TMS, CDCl$_3$, ppm) 0.92(3H, t, J=6 Hz), 1.2–1.8(2H), 2.0–2.8(4H), 2.55(3H, s), 3.2–3.5(4H), 4.0–4.3(4H), 6.38 (1H, d, J=9 Hz), 7.56(1H, d, J=9 Hz), 12.7(1H).

EXAMPLE 4

Starting compound:

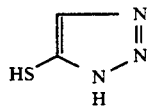

Desired compound: 2-Hydroxy-3-propyl-4-[3-[(1H-1,2,3-triazol-4-yl)thio]propoxy]acetophenone

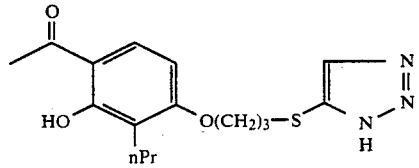

Physicochemical properties:
i) Oily product
ii) Nuclear magnetic resonance spectra (TMS, CDCl$_3$, ppm) 0.8–1.1(3H), 1.2–1.8(2H), 2.0–2.8(5H), 2.55 (3H, s), 3.0–3.2(1H), 3.9–4.3(2H), 4.5–4.7 (1H), 6.3–6.4(1H), 7.5–7.6(2H), 12.8(1H)

EXAMPLE 5

Starting compound:

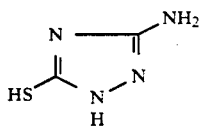

Desired compound: 4-[3-[(5-Amino-2H-1,2,4-triazol-3-yl)thio]propoxy]-2-hydroxy-3-propylacetophenone

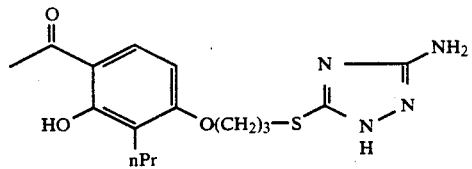

Physicochemical properties:
i) Melting point: 171° to 172° C.

| ii) Elemental analysis for C$_{16}$H$_{22}$N$_4$O$_3$S: | | | |
|---|---|---|---|
| | C | H | N |
| Calculated: | 54.84% | 6.33% | 15.99% |
| Found: | 55.07% | 6.62% | 15.77% |

EXAMPLE 6

Starting compound:

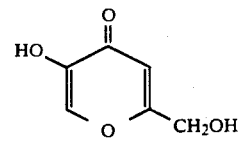

Desired compound: 2-Hydroxy-4-[3-[(6-hydroxymethyl-4-oxo-4H-pyran-3-yl)oxy]propoxy]-3-propylacetophenone

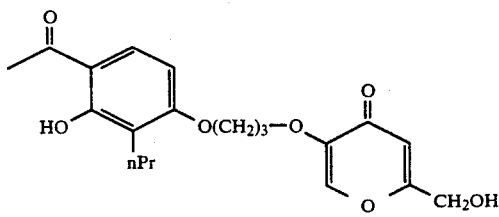

Physicochemical Properties:
i) Melting point: 84° to 87° C.

| ii) Elemental analysis for C$_{20}$H$_{24}$O$_7$: | | |
|---|---|---|
| | C | H |
| Calculated: | 63.82% | 6.43% |
| Found: | 63.73% | 6.67% |

EXAMPLE 7

Starting compound:

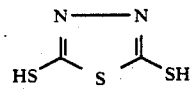

Desired compound: 2-Hydrocy-4-[[3-(5-mercapto-1,3,4-thiadiazol-2-yl)thio]propoxy]-3-propylacetophenone

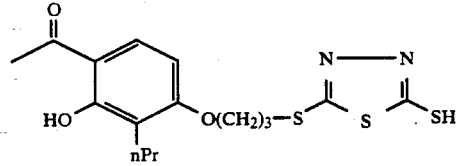

Physicochemical Properties:
i) Melting point: 127° to 129° C.

| ii) Elemental analysis for C$_{16}$H$_{20}$N$_2$O$_3$S$_3$: | | | | |
|---|---|---|---|---|
| | C | H | N | S |
| Calculated: | 49.97% | 5.24% | 7.28% | 25.02% |
| Found: | 50.00% | 5.33% | 7.19% | 24.82% |

EXAMPLE 8

Starting compound:

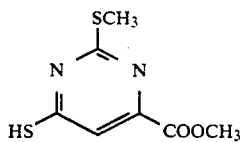

Desired compound: Methyl 6-[[3-(4-acetyl-3-hydroxy-2-propylphenoxy)propyl]thio]-2-methylthio-4-pyrimidinecarboxylate

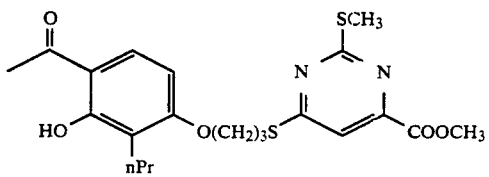

Physicochemical properties:
i) Melting point: 99° to 100° C.
ii) Nuclear magnetic reasonace spectra (TMS, CLCl₃, ppm) 1.93 (3H, t, J=6 Hz), 1.3-1.7(2H), 2.0-2.8(4H), 2.55(3H, s), 2.58 (3H, s), 3.3-3.5(2H), 3.92 (3H, s), 4.0-4.3(2H), 6.4-7.7(3H), 12.7(1H)

EXAMPLE 9

Starting compound:

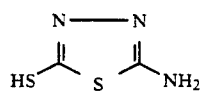

and compound of reference example 12
Desired compound: 4-[4-[(2-Amino-1,3,4-thiadiazol-5-yl)thio]butoxy]-2-hydroxy-3-propylacetophenone

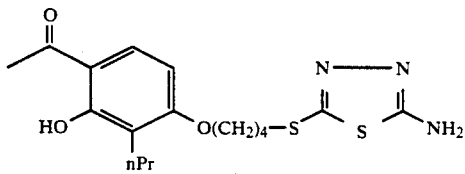

Physicochemical properties:
i) melting point: 107° to 108° C.

| ii) Elemental analysis for C₁₇H₂₃N₃O₃S₂: | | | | |
|---|---|---|---|---|
| | C | H | N | S |
| Calculated: | 53.52% | 6.08% | 11.01% | 16.81% |
| Found: | 53.24% | 5.89% | 10.97% | 16.74% |

EXAMPLE 10

Starting compound:

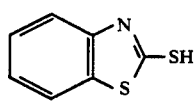

Desired compound: 4-[3-(2-Benzothiazolylthio)propoxy]-2-hydroxy-3-propylacetophenone

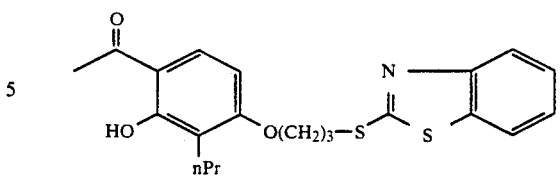

Physicochemical properties:
i) Oily product

| ii) Elemental analysis for C₂₁H₂₃NO₃S₂: | | | |
|---|---|---|---|
| | C | H | N |
| Calculated: | 62.81% | 5.77% | 3.49% |
| Found: | 62.98% | 5.98% | 3.36% |

EXAMPLE 11

Starting compound:
Compound of Reference Example 2
Desired compound: Ethyl 4-[[5-[[3-(4-acetyl-3-hydroxy-2-propylphenoxy)propyl]thio]-1,3,4-thiadiazol-2-yl]thio]butyrate

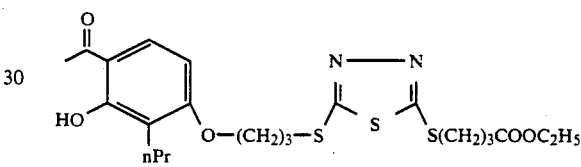

Physicochemical properties:
i) Oily product

| ii) Elemental analysis for C₂₂H₃₀N₂O₅S₃: | | | | |
|---|---|---|---|---|
| | C | H | N | S |
| Calculated: | 52.99% | 6.06% | 5.62% | 19.29% |
| Found: | 52.99% | 6.11% | 5.53% | 19.18% |

EXAMPLE 12

Starting compound:

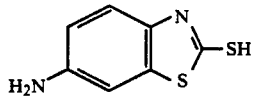

Desired compound: 4-[3-[(6-Aminobenzothiazol-2-yl)thio]propoxy]-2-hydroxy-3-propylacetophenone

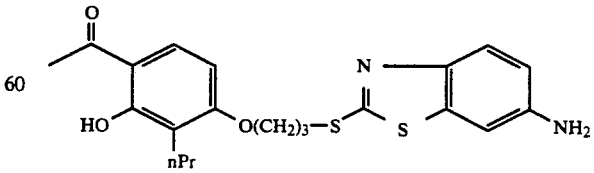

Physicochemical properties:
i) Oily product
ii) Nuclear magnetic reasonacen spectra (CDCl₃, TMS, ppm) 1.95(s, 3H), 1.2-2.0(2H,), 2.53(s, 3H), 2.0–2.9(4H), 4.48(t, 3H), 3.4–4.0(2H, —NH₂), 4.17(t, 3H), 6.2–7.8(5H), 12.70(1H)

EXAMPLE 13

Starting compound:

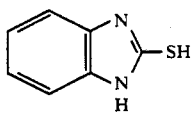

Desired compound: 4-[3-(2-Benzimidazolylthio)-propoxy]-2-hydroxy-3-propylacetophenone

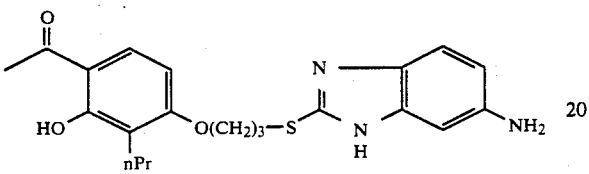

Physicochemical Properties:
i) Melting point: 143° to 146° C.

| ii) Elemental analysis for C$_{21}$H$_{24}$N$_2$O$_3$S: | | |
|---|---|---|
| | C | H | N |
| Calculated: | 65.60% | 6.29% | 7.29% |
| Found: | 65.46% | 6.34% | 7.25% |

EXAMPLE 14

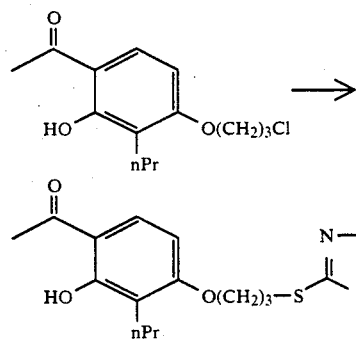

A mixture of 21.87 g of 4-(3-chloropropoxy)-2-hydroxy-3-propylacetophenone, 18.18 g of ethyl [(5-mercapto-1,3,4-thiadiazol-2-yl)thio]acetate, obtained in reference example 4 12.7 g of anhydrous potassium carbonate, and 80 ml of methyl ethyl ketone was refluxed for 2.5 hours with vigorous stirring. After cooling, insoluble matters were filtered off and the filtrate was concentrated under reduced pressure. To the residue thus formed were added 200 ml of ethyl acetate and 150 ml of toluene and the mixture was washed with a diluted aqueous solution of sodium hydroxide and water, dried over anhydrous magnesium sulfate, and then concentrated under reduced pressure. The residue thus obtained was applied to silica gel column chromatography and eluted with a mixture of toluene and ethyl acetate (10:1) to provide 33 g of ethyl [[5-[[3-(4-acetyl-3-hydroxy-2-propylphenoxy)propyl]thio]-1,3,4-thiadiazol-2-yl]thio]acetate.
Melting point: 71° to 72.5° C.

| Elemental analysis for C$_{20}$H$_{26}$N$_2$O$_5$S$_3$: | | | | |
|---|---|---|---|---|
| | C | H | N | S |
| Calculated: | 51.04% | 5.57% | 5.95% | 20.44% |
| Found: | 51.07% | 5.49% | 5.79% | 20.17% |

EXAMPLES 15 TO 18

By following the same procedure as Example 14, the following compounds were prepared.

EXAMPLE 15

Starting compound:

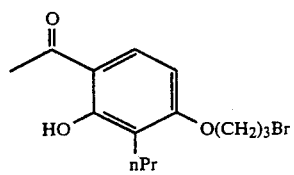

and the compound of Reference Example 5
Desired compound: Ethyl 5-[[5-[[3-(4-acetyl-3-hydroxy-2-propylphenoxy)propyl]thio]-1,3,4-thiadiazol-2-yl]thio]valerate

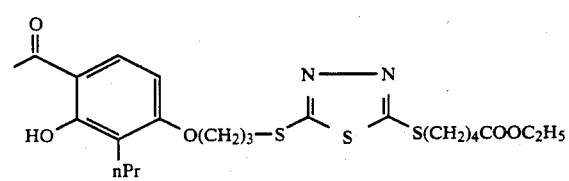

Physicochemical properties:
i) Oily product
ii) Nuclear magnetic resonance spectra (CDCl₃, TMS, ppm) 0.92(t, 3H), 1.24(t, 3H), 1.50–2.0(m, 6H), 2.34(2H), 2.54(s, 3H), 3.28(t, 2H), 3.46(t, 2H), 3.8–4.4(4H), 6.42(d, 1H), 7.58(d, 1H), 12.68(s, 1H)

EXAMPLE 16

Starting compound: Compound of Reference Example 6 and

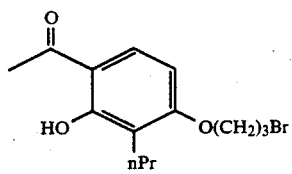

Desired compound: Ethyl 6-[[5-[[3-(4-acetyl-3-hydroxy-2-propylphenoxy)propyl]thio]-1,3,4-thiadiazol-2-yl]thio]hexanoate

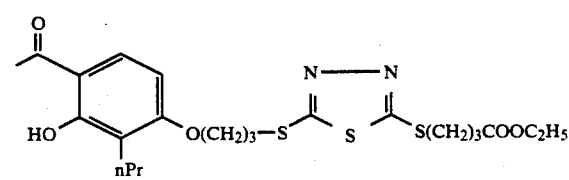

Physicochemical properties:

i) Oily product
ii) Nuclear magnetic reasonance spectra (CDCl₃, ppm) 0.92(t,3H), 1.24(t,3H), 1.3–2.0(8H), 2.1–2.5 (4H), 2.54(s, 3H), 3.28(t,2H), 3.48(t,2H), 4.0–4.3(4H), 6.43(d,1H), 7.60(d, 1H), 12.7 (s,1H)

EXAMPLE 17

Starting compound:

and Compound of Reference Example 8

Desired compound: Ethyl 2-[[5-[[3-(4-acetyl-3-hydroxy-2-propylphenoxy)propyl]thio]-1,3,4-thiadiazol-2-yl]thio]propionate Physicochemical properties:
i) Oily product

| Elemental analysis for C₂₁H₂₈N₂O₅S₃: | | |
|---|---|---|
| | N | S |
| Calculated: | 5.78% | 19.85% |
| Found: | 5.85% | 20.05% |

EXAMPLE 18

Starting compound:

and

COMPOUND OF REFERENCE EXAMPLE 7

Desired compound: Ethyl 4-[[5-[[3-(4-acetyl-3-hydroxy-2-propylphenoxy)propyl]thio]-1,3,4-thiadiazol-2-yl]thio]valerate Physicochemical properties:
i) Oily product
ii) Nuclear magnetic reasonance spectra (CDCl₃, TMS, ppm) 0.97(t,3H), 1.26(t,3H), 1.50 (d, 3H), 1.4–1.80(2H), 2.36(t,2H), 2.60(s, 3H), 3.52 (t, 2H), 3.90(q,1H), 4.0–4.4(4H), 6.46(d,1H), 7.63(d,1H0, 12.7(s, 1H)

EXAMPLE 19

By following the same procedure as Example 14 using 0.45 g of 2,4-dihdyroxy-3-propylacetophenone and 0.75 g of ethyl [[5-(3-bromopropyl)thio-1,3,4-thiadiazol-2-yl]thio]acetate as the raw materials, 0.2 g of ethyl [[5-[[3-(4-acetyl-3-hydroxy-2-propylphenoxy)-propyl]thio]-1,3,4-thiadiazol-2-yl]thio]acetate. The properties of the product obtained were same as those of the product obtained in Example 14.

EXAMPLE 20

A mixture of 596 mg of 4-(3-bromopropoxy)-2-hydroxy-3-propylacetophenone, 372.4 mg of ethyl [(5-mercapto-1,3,4-thiadiazol-2-yl)thio]acetate, obtained in reference example 4 326 mg of anhydrous potassium carbonate, and 5 ml of N,N-dimethylformamide was stirred for 2 hours at room temperature. The reaction mixture thus obtained was concentrated under reduced pressure and after addition of chloroform, the mixture was washed with water, dried over anhydrous magnesium sulfate, and concentrated under reduced pressure. The residue thus formed was applied to silica gel column chromatography and eluted with a mixture of toluene and ethyl acetate (10:1) to provide 663.3 mg of ethyl [[5-[[3-(4-acetyl-3-hydroxy-2-propoxyphenoxy)-propyl]thio]-1,3,4-thiadiazol-2-yl]thio]acetate. The properties of the compound thus obtained were same as those of the compound obtained in Example 14.

EXAMPLE 21

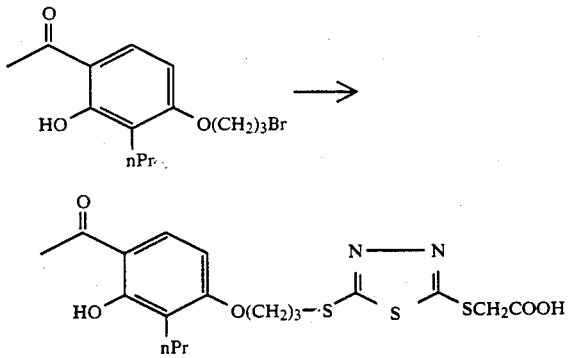

A mixture of 3.1 g of 4-(3-bromopropoxy)-2-hydroxy-3-propylacetophenone, 2.4 g of [(5-mercapto-1,3,4-thiadiazol-2-yl)thio]acetic acid, obtained in reference example 1 3 g of potassium carbonate, and 30 ml of N,N-dimethylformamide was stirred for 3 hours at room temperature. After addition of 150 ml of water to the reaction mixture obtained, the product was extracted with ethyl acetate. The separated aqueous layer was acidified with 10% hydrochloric acid, and extracted with ethyl acetate. The extract was washed with water, dried over anhydrous magnesium sulfate, and then the solvent was distilled off under reduced pressure to provide a solid material. The solid material was recrystallized from ethanol to provide 2.5 g of [[5-[[3-(4-acetyl-3-hydroxy-2-propylphenoxy)propyl]thio]-1,3,4-thiadiazol-2-yl]thio]acetic acid.

Melting point: 129° to 130° C.

| Elemental analysis for $C_{18}H_{22}N_2O_5S_3$: | | | |
|---|---|---|---|
| C | H | N | S |
| Calculated: 48.85% | 5.01% | 6.33% | 21.74% |
| Found: 48.78% | 5.13% | 6.29% | 21.49% |

EXAMPLE 22

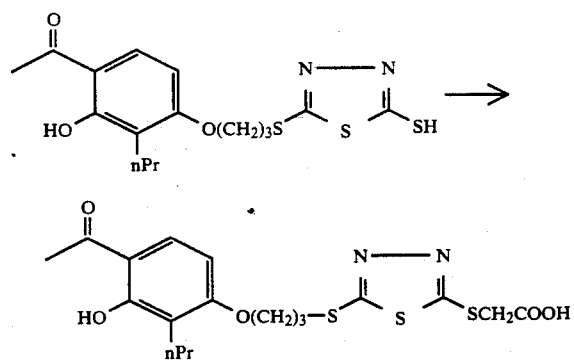

By following the same procedure as Example 21 using 100 mg of 2-hydroxy-4-[[-(5-mercapto-1,3,4-thiadiazol-2-yl)thio]propoxy]-3-propylacetophenone obtained in Example 7 and 40 mg of bromoacetic acid as the starting materials, 70 mg of [[5-[[3-(4-acetyl-3-hydroxy-2-propylphenoxy)propyl]-thio]-1,3,4-thiadiazol-2-yl]thio] acetic acid was obtained. The compound thus obtained had the same properties as those of the compound obtained in Example 21.

EXAMPLE 23

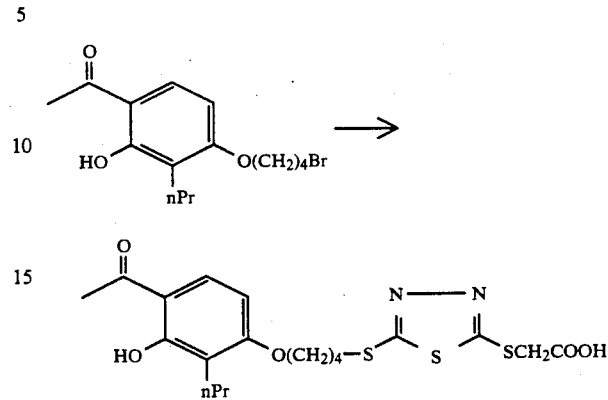

A mixture of 1.3 g of 4-(4-bromobutoxy)-2-hydroxy-3-propylacetophenone, obtained in Reference Example 12, 1.0 g of [5-mercapto-1,3,4-thiadiazol-2-yl)thio]acetic acid, 1.0 g of anhydrous potassium carbonate, and 5 ml of N,N-dimethylformamide was stirred for 3 hours at 50° C. The reaction mixture thus obtained was mixed with 30 ml of water, washed with toluene, acidified with diluted hydrochloric acid, and extracted with ethyl acetate. The extract thus formed was washed with water, dried over anhydrous magnesium sulfate, and concentrated under reduced pressure. The residue thus formed was recrystallized from ethyl acetate to provide 1.15 g of [[5-[[4-(4-acetyl-3-hydroxy-2-propylphenoxy)-butyl]thio]-1,3,4-thiadiazol-2-yl]thio]acetic acid.

Melting point: 123° to 124.5° C.

| Elemental analysis for $C_{19}H_{24}N_2O_5S_3$: | | | |
|---|---|---|---|
| C | H | N | S |
| Calculated: 49.98% | 5.30% | 6.14% | 21.07% |
| Found: 49.76% | 5.29% | 6.07% | 21.13% |

EXAMPLES 24 TO 27

By following same procedure as in Example 23, the following compounds were prepared.

EXAMPLE 24

Starting compound: The compound of Reference Example 1 and the compound of Reference Example 13

Desired compound: [[5-[[5-(4-Acetyl-3-hydroxy-2-propylphenoxy)pentyl]thio]-1,3,4-thiadiazol-2-yl]thio]acetic acid

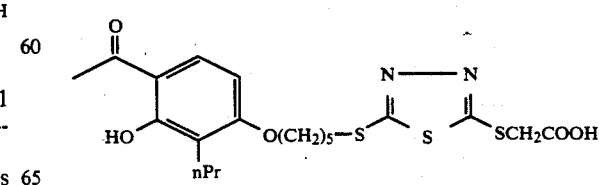

Physicochemical properties:
i) Melting point: 107° to 108° C.

| ii) Elemental analysis for $C_{20}H_{26}N_2O_5S_3$ | | | | |
|---|---|---|---|---|
| | C | H | N | S |
| Calculated: | 51.04% | 5.57% | 5.95% | 20.44% |
| Found: | 50.81% | 5.64% | 5.98% | 20.40% |

EXAMPLE 25

Starting compound: The compound of Reference Example 1 and the compound of Reference Example 11

Desired compound: [[5-[[2-(4-Acetyl-3-hydroxy-2-propylphenoxy)ethyl]thio]-1,3,4-thiadiazol-2-yl]thio]acetic acid

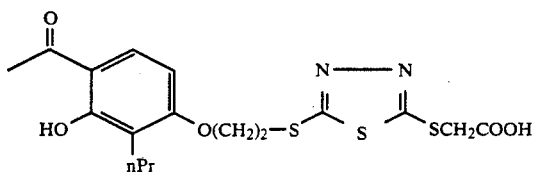

Physicochemical properties:
i) Melting point: 135° to 137° C.
ii) Nuclear magnetic resonance spectra (DMSO-$d_6$, TMS, ppm) 0.98(t, 3H), 1.44(m, 2H), 2.60(s, 3H), 3.72(t, 2H), 4.16(d, 2H), 4.40(t, 2H), 6.66 (d, 1H), 2.78(d, 1H), 12.81(s, 1H)

EXAMPLE 26

Starting compound:

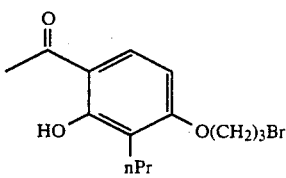

and Compound of Reference example 9

Desired compound: 3-[[5-[[3-(4-acetyl-3-hydroxy-2-propylphenoxy)propyl]thio]-1,3,4-thiadiazol-2-yl]thio]-propionic acid

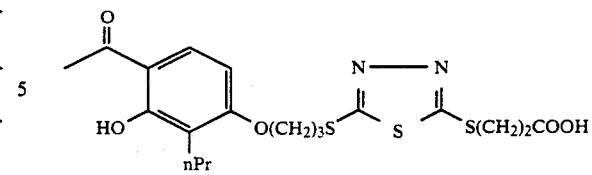

Physicochemical properties:
i) Melting point 102° to 104° C.

| ii) Elemental analysis for $C_{19}H_{24}N_2O_5S_3$: | | |
|---|---|---|
| | N | S |
| Calculated: | 6.14% | 21.06% |
| Found: | 6.28% | 21.03% |

EXAMPLE 27

Starting compound:

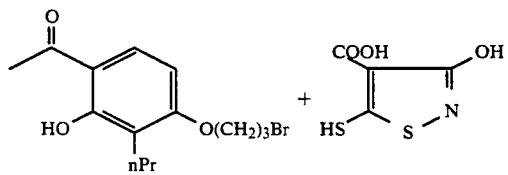

Desired compound: 5-[[3-(4-acetyl-3-hydroxy-2-propylphenoxy)propyl]thio]-3-hydroxy-4-isothiazol carboxylic acid

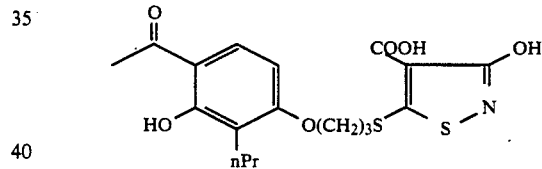

Physicochemical properties:
i) Melting point 182° to 184° C.

| ii) Elemental analysis for $C_{18}H_{21}NO_6S_2$: | | | | |
|---|---|---|---|---|
| | C | H | H | S |
| Calculated: | 52.54% | 5.14% | 3.40% | 15.58% |
| Found: | 52.23% | 4.96% | 3.20% | 15.48% |

EXAMPLE 28

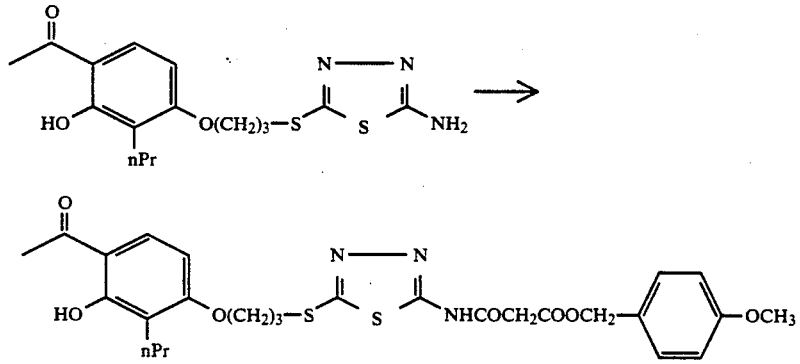

To a solution of 0.28 g of 4-[3-[(5-amino-1,3,4-thiadiazol-2-yl)thio]propoxy]-2-hydroxy-3-propylacetophenone obtained in Example 2 dissolved in 5 ml of pyridine were added 0.28 g of mono-p-methoxybenzyl malonate, 0.20 g of dicyclohexylcarbodiimide, and 10 mg of p-toluenesulfonic acid, and the mixture obtained was stirred for 3 hours at room temperature. Insoluble matters were filtered off and the filtrate obtained was concentrated under reduced pressure. To the residue thus formed was added 30 ml of water and the product was extracted with 20 ml of toluene. The extract thus obtained was washed with water, dried over anhydrous magnesium sulfate, and then the solvent was distilled off to provide a solid material. The solid material was washed with methanol and dried to provide 0.25 g of p-methoxybenzyl 3-[[5-[[3-(4-acetyl-3-hydroxy-2-porpylphenoxy)propyl]thio]-1,3,4-thiadiazol-2-yl]amino]-3-oxopropionate.

Melting point: 133° to 135° C.

| Elemental analysis for $C_{27}H_{31}N_3O_7S_2$: | | | | |
|---|---|---|---|---|
| | C | H | N | S |
| Calculated: | 56.53% | 5.45% | 7.32% | 11.18% |
| Found: | 56.81% | 5.46% | 7.19% | 10.96% |

EXAMPLES 29 TO 32

By following the same manner as in Example 28, the following compounds were prepared.

EXAMPLE 29

Starting compound: Compound of Example 2 and

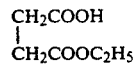

Desired compound: Ethyl 4-[[5-[[3-(4-acetyl-3-hydroxy-2-propylphenoxy)propyl]thio]-1,3,4-thiadiazol-2-yl]amino]-4-oxobutyrate

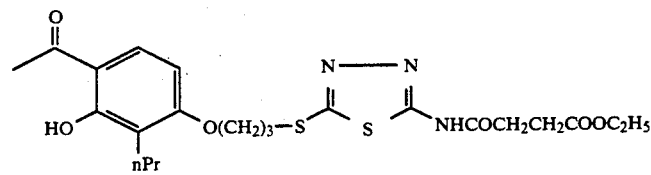

Physicochemical properties:
i) Melting point: 129° to 131° C.

| ii) Elemental analysis for $C_{22}H_{29}N_3O_6S_2$: | | | |
|---|---|---|---|
| | C | H | N |
| Calculated: | 53.32% | 5.90% | 8.48% |
| Found: | 53.14% | 5.76% | 8.47% |

EXAMPLE 30

Starting compound: Compound of Example 9 and

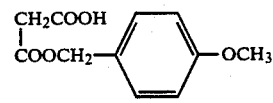

Desired compound: p-Methoxybenzyl 3-[[5-[[4-(4-acetyl-3-hydroxy-2-propylphenoxy)butyl]-thio]-1,3,4-thiadiazol-2-yl]amino]-3-oxopropionate

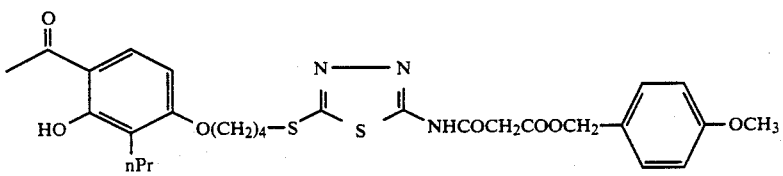

Physicochemical properties:
i) Melting point 141° to 143° C.
ii) Nuclear magnetic reasonance spectra (CDCl3, TMS, ppm) 1.90(t,3H), 1.0-2.0(8H), 2.60(s, 3H), 3.1-3.4(2H), 3.68(s,2H), 3.80(s,3H), 3.9-4.2 (2H), 5.12(s,2H), 6.15-7.4(7H), 12.7(s,1H)

EXAMPLE 31

Starting compound: Compound of example 5 and

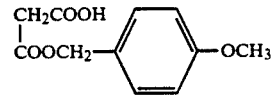

Desired compound: p-Methoxybenzyl 3-[[2-[[3-(4-acetyl-3-hydroxy-2-propylphenoxy)propyl]-thio]-1H-1,2,4-triazol-3-yl]amino]-3-oxopropionate

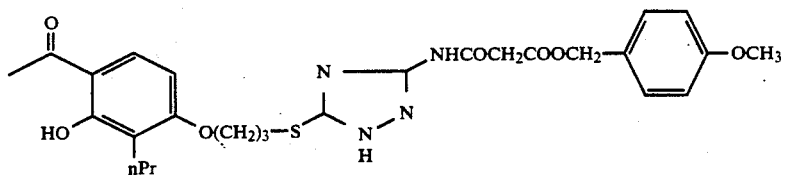

Physicochemical properties:

i) Melting point: 151° to 153° C.

ii) Elemental analysis for $C_{27}H_{32}N_4O_7S$:

| | C | H | N |
|---|---|---|---|
| Calculated: | 58.26% | 5.79% | 10.07% |
| Found: | 58.24% | 5.83% | 9.90% |

EXAMPLE 32

Starting compound: Compound of Example 12 and

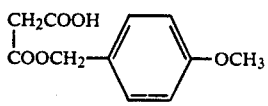

Desired compound: p-Methoxybenzyl 3-[[2-[[3-(4-acetyl-3-hydroxy-2-propylphenoxy)propyl]-thio]benzothiazol-6-yl]amino]-3-oxopropionate

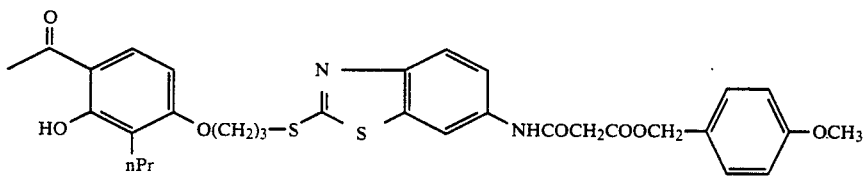

Physicochemical properties:
i) Melting point: 103° to 105° C.

ii) Elemental analysis for $C_{32}H_{34}N_2O_7S_2$:

| | C | H | N |
|---|---|---|---|
| Calculated: | 61.72% | 5.50% | 4.50% |
| Found: | 61.77% | 5.44% | 4.39% |

EXAMPLE 33

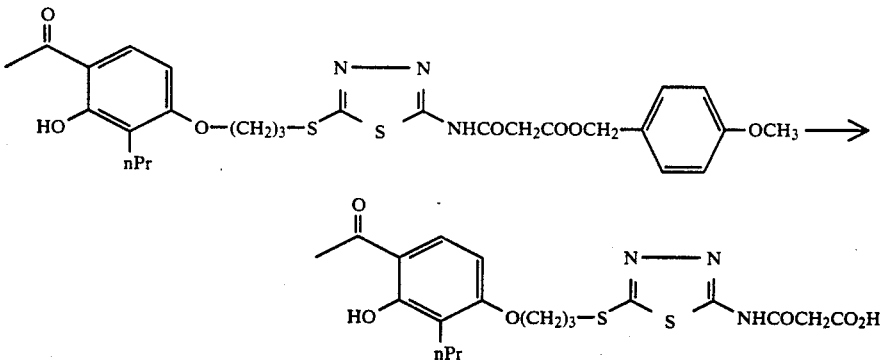

In a solution of 1.5 g of potassium hydroxide dissolved in 30 ml of 90% methanol was dissolved 0.9 g of p-methoxybenzyl ester obtained in Example 28 and the mixture was allowed to stand for 30 minutes at room temperature, 30 ml of water was added to the reaction mixture thus obtained. Then, methanol was distilled off from the reaction mixture and the aqueous solution thus obtained was washed with 30 ml of ethyl acetate, acidified with 10% hydrochloric acid, and then extracted with 30 ml of ethyl acetate. The extract thus obtained was washed with water, dried over anhydrous magnesium sulfate, and then the solvent was distilled off to provide a solid material. The solid material was washed with chloroform and dried to provide 0.5 g of 3-[[5-[[3-(4-acetyl-3-hydroxy-2-propylphenoxy)propyl]thio]-1,3,4-thiadiazol-2-yl]amino]-3-oxopropionic acid.

Melting point: 172° to 174° C.

Elemental analysis for $C_{19}H_{23}N_3O_6S_2$:

| | C | H | N | S |
|---|---|---|---|---|
| Calculated: | 50.32% | 5.11% | 9.26% | 14.14% |
| Found: | 50.95% | 5.01% | 9.29% | 13.93% |

EXAMPLES 34 TO 39

By following the same manner as Example 33, the following compounds were prepared.

EXAMPLE 34

Starting compound: The compound of Example 29
Desired compound: 4-[[5-[[3-(4-Acetyl-3-hydroxy-2-propylphenoxy)propyl]thio]-1,3,4-thiadiazol-2-yl]amino]-4-oxobutyric acid

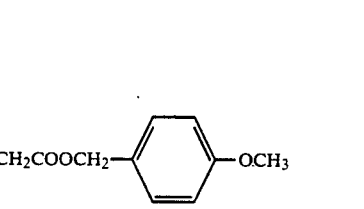

Physicochemical properties:

i) Melting point: 204° to 206° C.

ii) Elemental analysis for $C_{20}H_{25}N_3O_6S_2$:

| | C | H | N |
|---|---|---|---|
| Calculated: | 51.38% | 5.39% | 8.99% |
| Found: | 51.18% | 5.37% | 8.99% |

EXAMPLE 35

Starting compound: The compound of Example 30

Desired compound: 3-[[5-[[4-(4-Acetyl-3-hydroxy-2-propylphenoxy)butyl]thio]-1,3,4-thiadiazol-2-yl]amino]-3-oxopropionic acid.

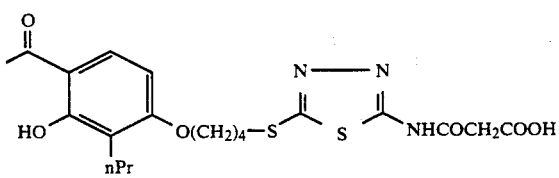

Physicochemical property:
i) Melting point: 168° to 170° C.

| ii) Elemental analysis for $C_{20}H_{25}N_3O_6S_2$: | | |
|---|---|---|
| | C | H |
| Calculated: | 51.38% | 5.39% |
| Found: | 51.60% | 5.68% |

EXAMPLE 36

Starting compound: The compound of Example 46
Desired compound: N-[5-[[3-(4-Acetyl-3-hydroxy-2-propylphenoxy)propyl]thio]-1,3,4-thiadiazol-2-yl]oxamic acid

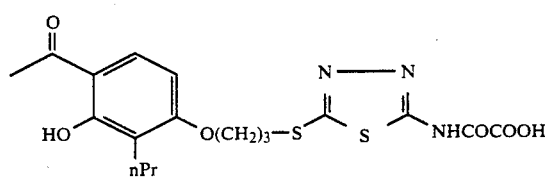

Physicochemical properties:
i) Melting point: 172° to 175° C. (decompd.)

| ii) Elemental analysis for $C_{18}H_{21}N_3O_6S_2$: | | |
|---|---|---|
| | C | H | N |
| Calculated: | 49.19% | 4.82% | 9.56% |
| Found: | 49.28% | 4.80% | 9.43% |

EXAMPLE 37

Starting compound: Compound of Example 8
Desired compound: 6-[[3-(4-Acetyl-3-hydroxy-2-propylphenoxy)propyl]thio]-2-methylthio-4-pyrimidinecarboxylic acid

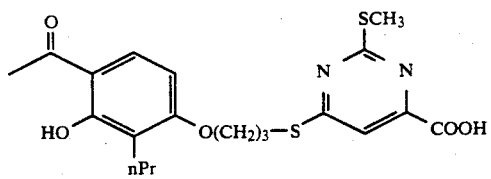

Physicochemical properties:
i) Melting point: 125° to 128° C.
ii) Nuclear magnetic reasonance spectra (TMS, $CDCl_3$ ppm) 0.92 (3H, t, J=6 Hz), 1.2–1.8(2H), 2.1–2.8 (4H), 2.55(3H, s), 2.59(3H, s), 3.3.–3.6(2H) 4.1–4.3(2H), 6.42(1H, d, J=9 Hz), 7.5–7.7(2H)

EXAMPLE 38

Starting compound: Compound of Example 11
Desired compound: 4-[[5-[[3-(4-Acetyl-3-hydroxy-2-propylphenoxy)propyl]thio]-1,3,4-thiadiazol-2-yl]thio]-butyric acid

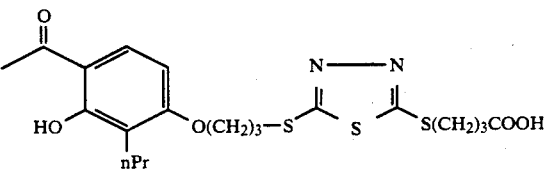

Physicochemical properties:
i) Melting point: 100° to 101° C.

| ii) Elemental analysis for $C_{20}H_{26}N_2O_5S_3$: | | | |
|---|---|---|---|
| | C | H | N | S |
| Calculated: | 51.04% | 5.57% | 5.95% | 20.44% |
| Found: | 51.18% | 5.66% | 5.74% | 20.44% |

EXAMPLE 39

Starting compound: Compound of Example 32
Desired compound: 3-[[2-[[3-(4-Acethyl-3-hydroxy-2-propylphenoxy)propyl]thio]benzothiazol-6-yl]amino]-3-oxopropionic acid

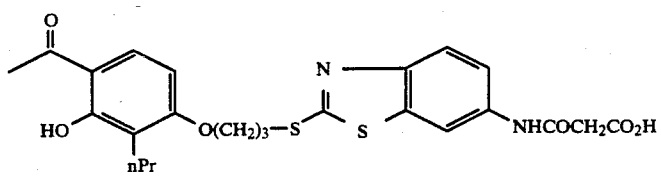

Physicochemical Properties:
i) Melting point: 148° to 150° C.

| ii) Elemental analysis for $C_{24}H_{26}N_2O_6S_2$: | | |
|---|---|---|
| | C | H | N |
| Calculated: | 57.35% | 5.21% | 5.57% |
| Found: | 57.18% | 5.19% | 5.56% |

EXAMPLE 40

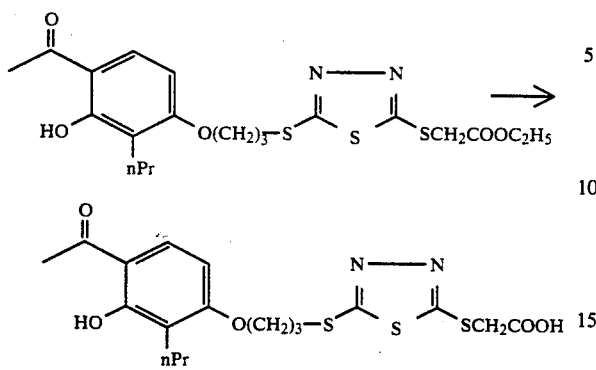

To a mixture of 4.2 g of ethyl [[5-[[3-(4-acetyl-3-hydroxy-2-propylphenoxy)propyl]thio]-1,3,4-thiadiazol-2-yl]thio]acetate obtained in Example 14 and 30 ml of methanol was added 20 ml of an aqueous solution of 5% sodium hydroxide and the mixture was stirred for 30 minutes. Then, 30 ml of water was added to the reaction mixture and methanol was removed under reduced pressure. The residue thus formed was washed with ethyl acetate, acidified with diluted hydrochloric acid, and extracted with ethyl acetate. The extract was washed with water, dried over anhydrous magnesium sulfate, and concentrated under reduced pressure. The residue thus formed was recrystallized from 90% ethanol to provide 3.07 g of [[5-[[3-(4-acetyl-3-hydroxy-2-propylphenoxy)propyl]thio]-1,3,4-thiadiazol-2-yl]thio]acetic acid. The properties of the compound thus obtained were same as those of the compound obtained in Example 21.

EXAMPLES 41 TO 45

EXAMPLE 41

By following the same procedure as Example 40, the following compounds were prepared.

EXAMPLE 41

Starting compound: The compound of Example 15
Desired compound: 5-[[5-[[3-(4-Acetyl-3-hydroxy-2-propylphenoxy)propyl]thio]-1,3,4-thiadiazol-2-yl]thio]-valeric acid

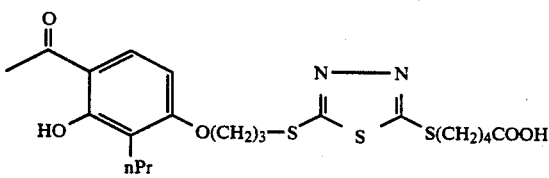

Physicochemical properties:
i) Melting point 86° to 87° C.

| ii) Elemental analysis for $C_{21}H_{28}N_2O_5S_3$: | | | | |
|---|---|---|---|---|
| | C | H | N | S |
| Calculated: | 52.04% | 5.82% | 5.78% | 19.85% |
| Found: | 51.82% | 6.02% | 5.72% | 19.96% |

EXAMPLE 42

Starting compound: The compound of Example 16
Desired compound: 6-[[5-[[3-(4-Acetyl-3-hydroxy-2-propylphenoxy)propyl]thio]-1,3,4-thiadiazol-2-yl]thio]-hexanoic acid

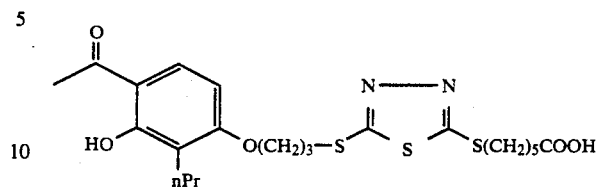

Physicochemical properties:
i) Melting point: 77° to 78° C.

| ii) Elemental analysis for $C_{22}H_{30}N_2O_5S_3.\tfrac{1}{4}H_2O$ | | | |
|---|---|---|---|
| | C | H | N |
| Calculated: | 52.15% | 5.97% | 5.53% |
| Found: | 52.14% | 6.21% | 5.33% |

EXAMPLE 43

Starting compound: Compound of Example 17
Desired compound: Sodium 2-[[5-[[3-(4-acetyl-3-hydroxy-2-propylphenoxy)propyl]thio]-1,3,4-thiadiazol-2-yl]thio]propionic acid

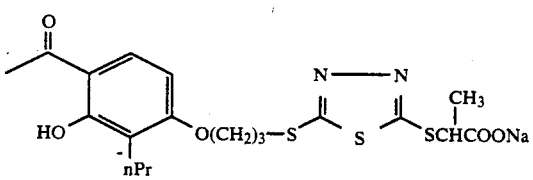

Physicochemical properties:
i) Oily product
ii) Nuclear magnetic reasonance spectra (DMSO-d$_6$, TMS, ppm) 0.88(t,3H), 1.52(d,3H), 2.20(2H), 2.60(s,3H), 3,44(t,2H), 4.22(t,2H), 6.66(d,1H), 7.84(d,1H), 12.8(s,1H),

EXAMPLE 44

Starting compound: Compound of Example 18
Desired compound: 4-[[5-[[3-(4-Acetyl-3-hydroxy-2-propylphenoxy)propyl]thio]-1,3,4-thiadiazol-2-yl]thio]-valeric acid

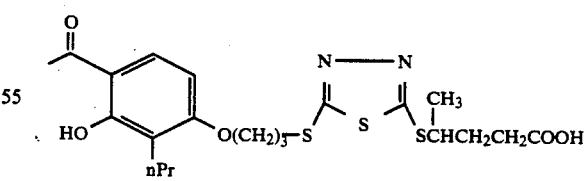

Physicochemical Properties:
i) Oily product
ii) Nuclear magnetic reasonance spectra (CDCl$_3$, TMS, ppm) 0.92(t, 3H), 1.49(d,3H), 2.12(t, 2H), 2.60 (s, 3H), 3.50(t,2H), 4.18(t, 2H), 6.45(d,1H), 7.61(d,1H), 12.7(s,1H)

EXAMPLE 45

Starting compound: Compound of Example 50

Desired compound: [[5-[2-(4-Acetyl-3-hydroxy-2-propylphenoxy)acetamide]-1,3,4-thiadiazol-2-yl]thio]acetic acid

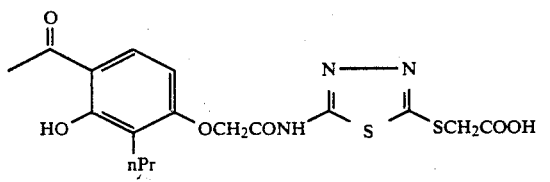

Physicochemical Properties:
i) Melting point: 224° to 226° C.

| ii) Elemental analysis for $C_{17}H_{19}N_3O_6S_2$: | | | | |
|---|---|---|---|---|
| | C | H | N | S |
| Calculated: | 47.99% | 4.50% | 9.88% | 15.07% |
| Found: | 47.97% | 4.41% | 9.76% | 14.94% |

EXAMPLE 46

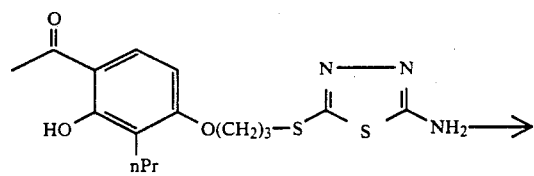

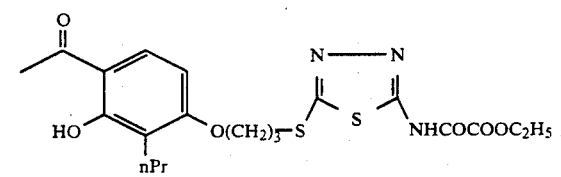

To a solution of 0.4 g of 4-[3-[(5-amino-1,3,4-thiadiazol-2-yl)thio]propoxy]-2-hydroxy-3-propylacetophenone obtained in Example 2 dissolved in 10 ml of pyridine was added a mixture of 0.2 g of ethyloxalyl chloride and 1 ml of toluene under cooling below −10° C. and then the resultant mixture was stirred for 30 minutes at room temperature. The reaction mixture thus obtained was mixed with 50 ml of water and extracted with 30 ml of ethyl acetate. The extract was successively washed with water, 5% hydrochloric acid, and then water, dried, and then the solvent was distilled off under reduced pressure. The residue thus formed was applied to silica gel column chromatography and eluted with a mixture of toluene and ethyl acetate (3:2) to provide 0.3 g of ethyl N-[5-[[3-(4-acetyl-3-hydroxy-2-propylphenoxy)propyl]thio]-1,3,4-thiadiazol-2-yl]oxamate.

Melting point: 146° to 147° C.

| ii) Elemental analysis for $C_{18}H_{21}O_6N_3S_2$: | | | | |
|---|---|---|---|---|
| | C | H | N | S |
| Calculated: | 49.19% | 4.82% | 9.56% | 14.59% |
| Found: | 49.28% | 4.80% | 9.43% | 14.56% |

EXAMPLE 47

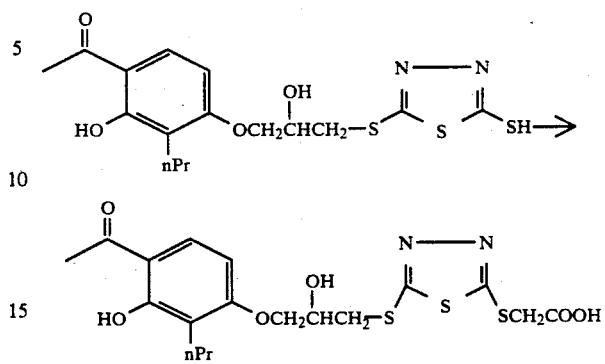

By following the same procedure as Example 22 using 2-hydroxy-4-[2-hydroxy-3-[(5-mercapto-1,3,4-thiadiazol-2-yl)thio]propoxy]-3-propylacetophenone obtained in Example 1 and bromoacetic acid as the starting materials, [[5-[[3-(4-acetyl-3-hydroxy-2-propylphenoxy)-2-hydroxypropyl]thio]-1,3,4-thiadiazol-2-yl]thio]acetic acid was obtained. Melting point: 72° to 75° C.

Nuclear magnetic resonance spectra (CDCl₃, TMS internal standard, ppm) 0.92(t, 3H), 1.3–1.8(m, 2H), 2.54(s, 3H), 2.60(t, 2H), 3,60(t, 2H), 4.04(s, 2H), 4.0–4.2(m, 2H), 4.2–4.6(m, 1H), 6.42(d, 1H), 7.60(d, 1H), 12.7(s, 1H).

EXAMPLE 48

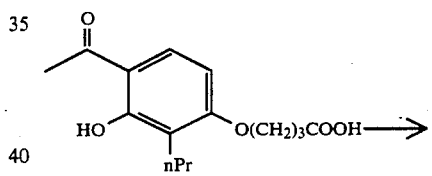

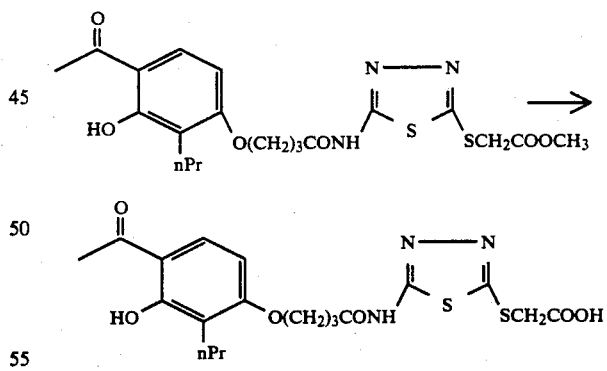

To a solution of 0.42 g of 4-(4-acetyl-3-hydroxy-2-propylphenoxy)butyric acid obtained in Reference Example 3 dissolved in 10 ml of pyridine were added 0.31 g of methyl [[5-amino-1,3,4-thiadiazol-2-yl)thio]acetate, 0.4 g of dicyclohexylcarbodiimide, and 3 mg of p-toluenesulfonic acid and the mixture was stirred for 3 hours at room temperature. Insoluble matters were removed by filtration and the filtrate was concentrated. The solid residue thus formed was, without being purified, dissolved in a solution of 1 g of potassium hydroxide dissolved in 20 ml of 90% methanol and after filtering off insoluble matters, the filtrate was allowed to stand for 30 minutes at room temperature. To the reaction mixture thus obtained was added 20 ml of water and then methanol was distilled off under reduced pressure. The aqueous solution thus obtained was washed with 20 ml of ethyl acetate. The aqueous solution was acidified with 10% hydrochloric acid and extracted with ethyl acetate. The extract thus obtained was washed with water, dried over anhydrous magnesium sulfate, and then the solvent was distilled off to provide 0.3 g of [[5-[[4-(4-acetyl-3-hydroxy-2-propylphenoxy)-butyrylamido]-1,3,4-thiadiazol-2-yl]thio]acetic acid.

Nuclear magnetic resonance spectra (CDCl$_3$, DMSO-d$_6$, ppm).

0.87(3H, t), 1.1–1.7(2H), 2.57(3H, s), 1.9–3.0(6H), 4.07(2H, s), 4.11(2H, t), 6.61(1H, d), 7.78(1H, d), 12.80(1H, s)

EXAMPLE 49

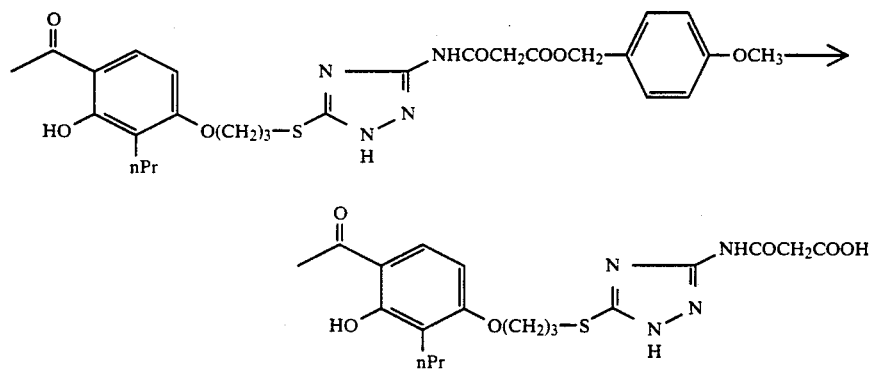

In a mixture of 1.5 ml of trifluoroacetic acid and 0.1 ml of anisole was dissolved 100 mg of p-methoxybenzyl 3-[[5-[[3-(4-acetyl-3-hydroxy-2-propylphenoxy)propyl]thio]-1H-1,2,4-triazol-3-yl]amino]-3-oxopropionate obtained in Example 31 at 10° to 20° C. and after stirring the solution thus obtained for 30 minutes, trifluoroacetic acid was distilled off under reduced pressure. The residue thus formed was mixed with 20 ml of water and extracted with 20 ml of ethyl acetate. The extract was washed with water, dried over anhydrous magnesium sulfate, and then the solvent was distilled off to provide a solid product. The solid product was washed with methylene chloride and dried to provide 50 mg of 3-[[5-[[-3-(4-acetyl-3-hydroxy-2-propylphenoxy)propyl]thio]-1H-1,2,4-triazol-3-yl]amino]-3-oxopropionic acid.

Melting point: 163° to 165° C.

Nuclear magnetic resonance spectra (CDCl$_3$-DMSO-d$_6$ (10:1), TMS, ppm)

0.90(3H, t), 1.2–1.8(2H), 2.0–2.8(4H), 2.55(3H, s), 3.25(3H, t), 3.48(2H, s), 4.17(2H, t), 6.44(1H, d), 7.61(1H, d), 12.68(1H, s).

EXAMPLE 50

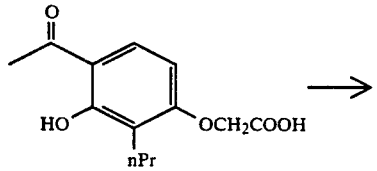

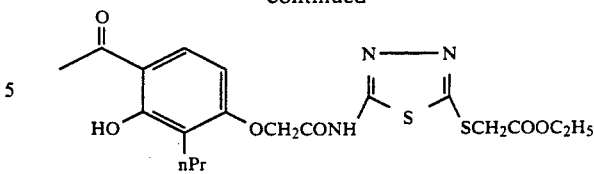

To a mixture of 0.7 g of (4-acetyl-3-hydroxy-2-propylphenoxy)acetic acid obtained in Reference Example 10, 0.6 g of ethyl [[5-amino-1,3,4-thiadiazol-2-yl]thio]acetate, 10 ml of pyridine, and 1 mg of p-toluenesulfonic acid was added 0.57 g of dicyclohexylcarbodiimide and the mixture was stirred for one hour at room temperature. Insoluble matters were filtered off and the filtrate formed was concentrated under reduced pressure. To the residue thus formed was added ethyl acetate and the mixture was washed with diluted hydrochloric acid, washed with diluted aqueous solution of sodium hydrogen carbonate, washed with water, dried over anhydrous magnesium sulfate, and concentrated under reduced pressure. The residue thus formed was recrystallized from 2-methoxyethanol to provide 0.8 g of [[5-[2-(4-acetyl-3-hydroxy-2-propylphenoxy)acetoamide]-1,3,4-thiadiazol-2-yl]thio]acetic acid.

Melting point: 183° to 184° C.

| Elemental analysis for C$_{19}$H$_{23}$N$_3$O$_6$S$_2$: | | | |
|---|---|---|---|
| | C | H | N | S |
| Calculated: | 50.32% | 5.11% | 9.26% | 14.14% |
| Found: | 50.47% | 5.14% | 9.24% | 14.38% |

EXAMPLE 51

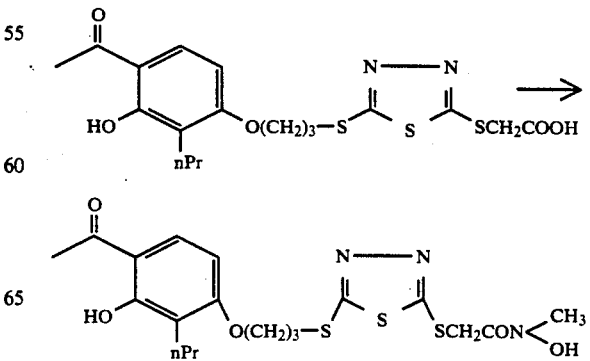

To a mixture of 0.5 g of [[5-[[3-(4-acetyl-3-hydroxy-2-propylphenoxy)propyl]thio]-1,3,4-thiadiazol-2-yl]thio]acetic acid, obtained in example 22 0.23 g of dicyclohexylcarbodiimide, 0.14 g of 1-hydroxybenzotriazole, and 50 ml of tetrahydrofuran was added a mixture of 0.27 g of N-methyl-hydroxylamine.hydrochloride, 0.3 g of triethylamine, and 5 ml of N,N-dimethylformamide and the resultant mixture was stirred overnight at room temperature. Then, insoluble matters were filtered off and the filtrate thus formed was concentrated under reduced pressure. To the residue thus formed was added 100 ml of ethyl acetate and the mixture was washed with water, washed with a diluted aqueous solution of sodium hydrogencarbonate, and water, dried over anhydrous magnesium sulfate, and concentrated under reduced pressure. To the residue thus obtained was added ethyl acetate, then insoluble materials were filtered off and the filtrate formed was concentrated. The residue thus obtained was recrystallized from a mixture of toluene and n-hexane to provide 0.18 g of 2-[[5-[[3-(4-acetyl-3-hydroxy-2-propylphenoxy)-propyl]thio]-1,3,4-thiadiazol-2-yl]thio]N-hydroxy-N-methylacetamide.

Melting point: 97° to 99° C.

| Elemental analysis for $C_{19}H_{25}N_3O_5S_3$: | |
|---|---|
| | N |
| Calculated: | 8.91% |
| Found: | 9.06% |

EXAMPLE 52

| (Tablet) | |
|---|---|
| Compound of Ex. 21 | 30 mg |
| Lactose | 104 mg |
| Corn starch | 57 mg |
| Hydroxypropyl cellulose | 4 mg |
| Calcium carboxymethyl cellulose | 4 mg |
| Magnesium stearate | 1 mg |
| total | 200 mg |

After uniformly mixing 30 g of compound of Ex. 21, 104 g of lactose and 57 g of corn starch, 40 ml of a 10% (w/w) aqueous solution of hydroxypropyl cellulose was added to the mixture and the resultant mixture was granulated by a wet granulation method. The granules thus obtained were mixed with 4 g of calcium carboxymethyl cellulose and 1 g of magnesium stearate and the mixture was press-tableted into tablet (200 mg per tablet).

EXAMPLE 53

| (Capsule) | |
|---|---|
| Compound of Ex. 21 | 30 mg |
| Crystalline cellulose | 40 mg |
| Crystalline lactose | 129 mg |
| Magnesium stearate | 1 mg |
| total | 200 mg |

The above components each in an amount 1000 times the foregoing amount were mixed and then filled in gelatin capsule to provide capsules (200 mg per capsule).

EXAMPLE 54

Inhalation

After dissolving 0.1 g of compound of Ex. 21 in about 90 ml of mixture of ethanol, propylene glycol and purified water (30:10:60 in weight ratio), the volume of the solution was adjusted to 100 ml using the aforesaid mixture and 10 ml each of the solution was filled in a definite container followed by sealing to provide an inhalation.

What is claimed is:

1. A heterocyclic compound represented by the following formula (I)

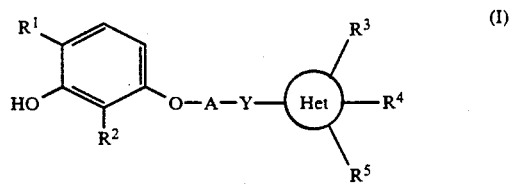

or a pharmaceutically acceptable salt thereof;
wherein $R^1$ represents a alkanoyl group; $R^2$ represents a $C_1$-$C_6$ alkyl group; A represents a lower $C_1$-$C_6$ alkylene group; Y represents an oxygen atom or a sulfur atom;
Het represents one ring selected from the group consisting of, a benzimidazole ring, a 1H-1,2,3-triazole ring, a 1H-1,2,4-triazole ring, a 2H-pyran ring and a 4H-pyran ring;
$R^3$, $R^4$, $R^5$, which may be the same or different, each represents a hydrogen atom, a $C_1$-$C_6$ alkyl group, a group shown by the formula $-A^1-R^6$ (wherein $A^1$ represents a $C_1$-$C_6$ alkylene group and R6 represents a hydroxy group), a hydroxy group, an oxo group, an amino group, a group shown by the formula $-NH-CO-R^9$ (wherein $R^9$ represents a carboxy-$C_1$-$C_6$ alkyl group, a $C_1$-$C_6$ alkoxycarbonyl $C_1$-$C_6$ alkyl group) or a carboxy group; however, when Het is a heterocyclic ring fused with a benzene ring, Y is bonded to the heterocyclic ring.

2. The heterocyclic compound or the pharmaceutically acceptable salt thereof as claimed in claim 1, wherein Y is sulfur and $R^3$, $R^4$ and $R^5$, which may be the same or different, each is a hydrogen atom, a group shown by the formula $-A^1-R^6$ (wherein, $R^6$ is a hydroxy group); a hydroxy group, an oxo group, an amino group, a group shown by the formula $-NH-CO-R^9$ wherein $R^9$ is as indicated.

3. A pharmaceutical composition useful as an antagonist of slow reacting substance of anaphylaxis (SRS-A) and containing as an individual adult dose amount, from 0.1 to 500 mg.k of the heterocyclic compound of claim 1.

4. The pharmaceutical composition as claimed in claim 3 wherein said pharmaceutical composition is capable of inhibiting the production and release of SRS-A.

5. A method of antagonizing the action of SRS-A in a host which comprises administering to said host a pharmaceutically effective amount of the composition of claim 3.

6. A method of inhibiting the production and release of SRS-A in a host which comprises administering to said host a pharmaceutically effective amount of the composition of claim 3.

7. The compound of claim 1 which is 3-[[5-[[3-(4-acetyl-3-hydroxy-2-propylphenoxy)propyl]thio]-1H,1,2,4-triazol-3-yl]amino]-3-oxopropionic acid or a pharmaceutically acceptable salt.

* * * * *